(12) United States Patent
Ulbrandt

(10) Patent No.: US 10,016,496 B2
(45) Date of Patent: Jul. 10, 2018

(54) RESPIRATORY SYNCYTIAL VIRUS F PROTEIN EPITOPES

(71) Applicant: MedImmune, LLC, Gaithersburg, MD (US)

(72) Inventor: Nancy Ulbrandt, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/764,635

(22) PCT Filed: Jan. 31, 2014

(86) PCT No.: PCT/US2014/014054
§ 371 (c)(1),
(2) Date: Jul. 30, 2015

(87) PCT Pub. No.: WO2014/121021
PCT Pub. Date: Aug. 7, 2014

(65) Prior Publication Data
US 2015/0366960 A1     Dec. 24, 2015

Related U.S. Application Data

(60) Provisional application No. 61/783,380, filed on Mar. 14, 2013, provisional application No. 61/759,664, filed on Feb. 1, 2013.

(51) Int. Cl.
| | | |
|---|---|---|
| *A61K 39/155* | (2006.01) | |
| *C07K 14/005* | (2006.01) | |
| *C07K 16/10* | (2006.01) | |
| *C12N 7/00* | (2006.01) | |

(52) U.S. Cl.
CPC .......... *A61K 39/155* (2013.01); *C07K 14/005* (2013.01); *C07K 16/1027* (2013.01); *C12N 7/00* (2013.01); *C07K 2317/34* (2013.01); *C07K 2317/76* (2013.01); *C07K 2319/00* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 8,562,996 | B2 | 10/2013 | Spits et al. |
| 8,568,726 | B2 | 10/2013 | Beaumont et al. |
| 9,060,975 | B2 | 6/2015 | de Haan et al. |
| 2002/0018780 | A1 | 2/2002 | Koenig et al. |
| 2010/0239593 | A1 | 9/2010 | Spits et al. |
| 2012/0070446 | A1 | 3/2012 | Beaumont et al. |
| 2014/0093500 | A1 | 4/2014 | Beaumont et al. |
| 2014/0271699 | A1 | 9/2014 | Kwong et al. |
| 2014/0377279 | A9 | 12/2014 | Spits et al. |

FOREIGN PATENT DOCUMENTS

| | | |
|---|---|---|
| WO | WO 2008/147196 A2 | 12/2008 |
| WO | WO 2009/128951 A2 | 10/2009 |
| WO | WO 2010/107847 A1 | 9/2010 |
| WO | WO 2011/043643 A1 | 4/2011 |
| WO | WO 2011/056899 A2 | 5/2011 |
| WO | WO 2012/089231 A1 | 7/2012 |
| WO | WO 2014/160463 A1 | 10/2014 |

OTHER PUBLICATIONS

Connors et al., Virology, 1995, 208(2):478-484.*
GenBank® Accession No. AAB86664.1, Jun. 30, 2004, Fusion F Glycoprotein Precursor, Human Respiratory Syncytial Virus.*
GenBank Accession No. P03420.1, Human Respiratory Syncytial Virus A2 F glycoprotein, 1986, 11 pages.*
U.S. Appl. No. 61/780,910, filed Mar. 13, 2013, McLellan et al.
U.S. Appl. No. 61/798,389, filed Mar. 15, 2013, McLellan et al.
International Search Report and Written Opinion for PCT/US2014/014054 issued by the U.S. Patent and Trademark office as the International Search Authority, dated Apr. 17, 2014.
International Preliminary Report on Patentability for PCT/US2014/014054, issued by WIPO, dated Aug. 4, 2015.
ATCC Product Sheet, "HEp-2 (ATCC® CCL-23™)," American Type Culture Collection, Manassas, VA; Jul. 19, 2013; 3 pgs.
ATCC Product Sheet, Human respiratory syncytial virus, Purified (ATCC® 1540™), American Type Culture Collection, Manassas, VA; Jan. 3, 2014; 2 pgs.
Beeler and Coelingh, "Neutralization epitopes of the F glycoprotein of respiratory syncytial virus: effect of mutation upon fusion function," *J of Virology*, Jul. 1989;63(7):2941-2950.
Christmann et al., "The cystine knot of a squash-type protease inhibitor as a structural scaffold for *Escherichia coli* cell surface display of conformationally constrained peptides." *Protein Eng*, 1999;12(9):797-806.
Huang et al., "Recombinant respiratory syncytial virus F protein expression is hindered by inefficient nuclear export and mRNA processing," *Virus Genes*, Apr. 2010;40(2):212-221.

(Continued)

*Primary Examiner* — Stacy B Chen
(74) *Attorney, Agent, or Firm* — Mueting, Raasch & Gebhardt, P.A.

(57) ABSTRACT

Respiratory Syncytial Virus is a common cold virus belonging to the family of paramyxovirus. RSV is virulent, easily transmissible and the most common cause of lower respiratory tract disease in children of less than 2 years of age. Up to 98% of children attending day care will be infected in a single RSV season. Between 0.5% and 3.2% of children with RSV infection require hospitalization. Approximately 90,000 hospital admissions and 4500 deaths per year were reported in United States. Major risk factors for hospitalization due to RSV are premature birth, chronic lung disease, congenital heart disease, compromised immunity, and age younger than 6 weeks in otherwise healthy children.

25 Claims, 15 Drawing Sheets

(56) References Cited

OTHER PUBLICATIONS

Karlin and Altschul, "Applications and statistics for multiple high-scoring segments in molecular sequences," *Proc Natl Acad Sci USA*, Jun. 1993;90(12):5873-5877.

McLellan et al., "Design and characterization of epitope-scaffold immunogens that present the motavizumab epitope from respiratory syncytial virus," *J Mol Biol*, Jun. 24, 2011;409(5):853-66. doi: 10.1016/j.jmb.2011.04.044. Epub Apr. 27, 2011.

McLellan et al., "Supplemental Materials for 'Design and characterization of epitope-scaffold immunogens that present the motavizumab epitope from respiratory syncytial virus,'" *J Mol Biol*, Jun. 24, 2011;409(5):853-66. 4 pgs.

McLellan et al., "Structural basis of respiratory syncytial virus neutralization by motavizumab," *Nat Struc Mol Bio*, Jan. 24, 2010;17(2):248-250.

McLellan et al., "Supplemental Materials for Structural basis of respiratory syncytial virus neutralization by motavizumab," *Nat Struc Mol Bio*, 2010; 13 pgs.

McLellan et al., "Structure of RSV Fusion Glycoprotein Trimer Bound to a prefusion-Specific Neutralizing Antibody," *Science*, Apr. 25, 2013;340(6136):1113-1117.

McLellan et al., "Supplemental Materials for 'Structure of RSV Fusion Glycoprotein Trimer Bound to a prefusion-Specific Neutralizing Antibody'," *Science Express*, Apr. 25, 2013; 18 pgs.

Yunus et al., "Elevated temperature triggers human respiratory syncytial virus F protein six-helix bundle formation," *Virology*, 2010;396(2):226-237.

Bolewska et al., "Synthesis, cloning and expression in *Escherichia coli* of a gene coding for the Met8→Leu CMTI I—a representative of the squash inhibitors of serine proteinases," *FEBS Letters*, 1995; 377:172-174.

Christmann et al., "The cystine knot of a squash-type protease inhibitor as a structural scaffold for *Escherichia coli* cell surface display of conformationally constrained peptides," Protein Engineering, 1999, 12(9):797-806.

Le-Nguyen et al., "Characterization and 2D NMR study of the stable [9-21, 15-27] 2 disulfide intermediate in the folding of the 3 disulfide trypsin inhibitor EETI II," *Protein Science*, 1993; 2:165-174.

Liu et al., "NMR studies of internal dynamics of serine proteinase protein inhibitors: Binding region mobilities of intact and reactive-site hydrolyzed *Cucurbita maxima* trypsin inhibitor (CMTI)-III of the squash family and comparison with those of counterparts of CMTI-V of the potato I family," *Protein Science*, 1998; 7:132-141.

Nielsen et al., An $^1$H NMR determination of the three-dimensional structures of mirror-image forms of a Leu-5 variant of the trypsin inhibitor from *Ecballium elaterium* (EETI-II), *Protein Science*, 1994; 3:291-302.

Otlewski and Krowarsch, "Squash inhibitor family of serine proteinases," *Acta Biochimica Polonica*, 1996; 43(3):431-444.

Pallaghy et al., "A common structural motif incorporating a cystine knot and a triple-stranded β-sheet in toxic and inhibitory polypeptides," *Protein Science*, 1994; 3:1833-1839.

\* cited by examiner

Antigenic Sites on RSV-F

Figure 6

AM23 binding site

| | F2 | | Deleted Peptide | | | | | | | | F1 | | | | | | |
|---|---|---|---|---|---|---|---|---|---|---|---|---|---|---|---|---|---|
| | 45 | 67 | 79 | 115 | 118 | 124 | 125 | 152 | 197 | 202 | 209 | 215 | 226 | 276 | 278 | 326 | 470 | 517 |
| 9320 | F | T | I | M | T | N | L | I | S | Q | Q | S | K | S | V | I | K | N |
| 18537 | F | T | I | M | T | N | L | I | N | R | Q | S | M | S | V | I | K | N |
| B1 | | | | | I | | | | N | Q | K | | K | | | | | |
| B5 | | | | | | | | | N | Q | Q | | K | | A | T | | |
| B15 | | | | | | | | | N | Q | Q | | K | | A | | | |
| B28 | | | | | | | | | N | Q | | | K | | A | T | | |
| B31 | | | | | | | | | N | Q | | | K | | | | | |
| A2 | L | N | I | M | T | K | T | V | N | Q | K | S | K | N | V | T | K | N |

Figure 8

RSV sequences in proposed antigenic site

| | | | | | | | | | | | | | | | | | | | | |
|---|---|---|---|---|---|---|---|---|---|---|---|---|---|---|---|---|---|---|---|---|
|195–|L|K|N|Y|I|D|K|Q|L|L|P|I|V|N|K|Q|S|C|S|I S-215|RSV-A2|
| |L|K|N|Y|I|D|K|Q|L|L|P|I|V|*Y*|K|Q|S|C|S|I S|RSV MARMS A1-A5|
| |L|K|N|Y|I|*N*|R|L|L|P|I|V|N|Q|Q|S|C|R|I|S|RSV MARM B1|
| |L|K|N|Y|I|N|R|L|*V*|P|I|V|N|Q|Q|S|C|R|I|S|RSV MARM B2/B3|
|195–|L|K|N|Y|I|N|R|L|L|P|I|V|N|Q|Q|S|C|R|I|S-215|RSV-B18537|

RESPIRATORY SYNCYTIAL VIRUS F PROTEIN EPITOPES

CONTINUING APPLICATION DATA

This application is the § 371 U.S. National Stage of International Application No. PCT/US2014/014054, filed 31 Jan. 2014, which claims the benefit of U.S. Provisional Application No. 61/759,664, filed 1 Feb. 2013 and U.S. Provisional Application No. 61/783,380, filed 14 Mar. 2013, each of which are incorporated by reference herein in their entireties.

REFERENCE TO SEQUENCE LISTING SUBMITTED ELECTRONICALLY

The content of the electronically submitted sequence listing in ASCII text file (Name: sequencelisting_ascii.txt; Size: 31.3 kilobytes; and Date of Creation: Mar. 14, 2013) filed with the application is incorporated herein by reference in its entirety.

BACKGROUND

Respiratory Syncytial Virus (RSV) is a common cold virus belonging to the family of paramyxovirus. RSV is virulent, easily transmissible and the most common cause of lower respiratory tract disease in children of less than 2 years of age. Up to 98% of children attending day care will be infected in a single RSV season. Between 0.5% and 3.2% of children with RSV infection require hospitalization. Approximately 90,000 hospital admissions and 4500 deaths per year were reported in United States. Major risk factors for hospitalization due to RSV are premature birth, chronic lung disease, congenital heart disease, compromised immunity, and age younger than 6 weeks in otherwise healthy children. No effective treatment of RSV positive bronchiolitis beside supportive care in the form of adequate nutrition and oxygen therapy is available. Antiviral therapies such as Ribavirin have not been proven to be effective in RSV infection. No vaccine is currently available for RSV prophylaxis.

The only RSV specific treatment available today is a humanized monoclonal antibody, palivizumab (also called SYNAGIS®), which is approved by the US Food and Drug Administration for the prevention of RSV lower respiratory disease in high-risk infants. However, palivizumab is not always effective. Another monoclonal antibody, motavizumab, also referred to herein as "mota", was derived from palivizumab with enhanced antiviral activity. Both palivizumab and motavizumab bind antigenic site A, a highly conserved region on the RSV-F protein between amino acids 258 and 275. It is known that most anti-F antibodies, including palivizumab and motavizumab, recognize an epitope that is shared by the two conformations in which RSV-F can fold, the metastable pre-fusion form and the highly stable post-fusion conformation.

The present disclosure provides a conformational epitope on the pre-fusion conformation of RSV-F protein, recognized by a recently identified anti-RSV monoclonal antibody D25, disclosed in WO 2008/147196. By targeting the pre-fusion RSV-F structure, which is the active target for inhibition of RSV-F mediated fusion, the present disclosure also provides a method for screening more effective anti-RSV antibodies which are less susceptible to non-productive binding events, hence may provide better prevention or treatment for RSV infections.

BRIEF SUMMARY

Provided herein is a conformational epitope on the surface of a respiratory syncytial virus fusion (RSV F) protein, where the epitope comprises at least 6 amino acids within amino acids 1 to 34 of SEQ ID NO:7 or amino acids 1 to 34 of SEQ ID NO:9, where an RSV F protein comprising the epitope can be specifically bound by monoclonal antibody D25 or an antigen-binding fragment, variant, analog or derivative thereof, provided that the RSV F protein is in pre-fusion conformation.

In one aspect, an RSV F protein in pre-fusion conformation comprising the epitope can be bound by monoclonal antibody D25, or a fragment, variant, analog, or derivative thereof with at least 100-fold greater affinity than an RSV F protein comprising the amino acid sequence of the F proteins derived from monoclonal antibody resistant mutants (MARMs), where the F proteins from the MARMs comprise the amino acid sequences of SEQ ID NO:12, SEQ ID NO:13, or SEQ ID NO:14. The epitope can appear on the surface of a human RSV subtype A F protein, and also on the surface of a human RSV subtype B F protein.

In certain aspects, binding of mAb D25 to the conformational epitope provided herein is altered or destroyed by various treatments known to destroy the pre-fusion conformation of RSV F protein, e.g., heating, long-term storage, fixation, or denaturation.

The conformational epitope provided herein is located C-terminal to the F protein heptad repeats.

Further provided is an isolated antigen-antibody structure comprising the conformational epitope described above; specifically bound to mAb D25 or an antigen-binding fragment, variant, analog, or derivative thereof. In certain aspects, the structure is a crystal structure.

Further provided is an isolated fusion protein comprising an RSV F protein fragment consisting essentially of amino acids 1 to 34 of SEQ ID NO:7 or amino acids 1 to 34 of SEQ ID NO:9; and a polypeptide scaffold, where the scaffold constrains the F protein fragment in a conformation that can be specifically bound by monoclonal antibody D25 or an antigen-binding fragment, variant, analog, or derivative thereof. In certain aspects, the scaffold is derived from a surface-exposed coat protein, e.g., a protease inhibitor such as a squash family protease inhibitor. In certain specific embodiments the scaffold is derived from the *Ecballium elaterium* trypsin inhibitor II (EETI-II). In certain aspects, the inhibitor loop of EETI-II is replaced by amino acids 1 to 34 of SEQ ID NO:7 or amino acids 1 to 34 of SEQ ID NO:9. In certain aspects, the fusion protein comprises the sequence of SEQ ID NO: 5.

Further provided is an isolated polynucleotide which encodes the fusion protein provided herein, an expression vector comprising the polynucleotide and/or a host cell comprising the polynucleotide or the vector.

In certain aspects, the fusion protein provided herein can be part of an immunogenic composition comprising the fusion protein and a carrier, excipient, and/or adjuvant.

In a further aspect the fusion protein provided herein can be used in a method for identifying anti-RSV F protein antibodies which bind to the conformational epitope provided herein, where the method comprises screening an antibody library for an antibody which binds to the fusion protein of any one of claims 9 to 15, but does not bind to the scaffold alone.

BRIEF DESCRIPTION OF THE DRAWINGS/FIGURES

FIG. 6 shows the known antigenic sites on RSV-F protein. RSV-F has at least six different commonly described neutralizing antigenic sites, including sites A/II, B/I, and C.

FIGS. 7A-D show the competition by known anti-RSV-F antibodies binding to the A/II, B/I, C, or an unknown site, respectively.

FIG. 8 shows that amino acid 209 is important for the neutralizing activity of antibody AM23.

FIG. 9 shows an alignment of RSV-F wild-type sequences and the D25 monoclonal antibody resistant mutants (MARMs) in the proposed D25 antigenic site. Boxed amino acids indicate the mutations.

Figure 10:
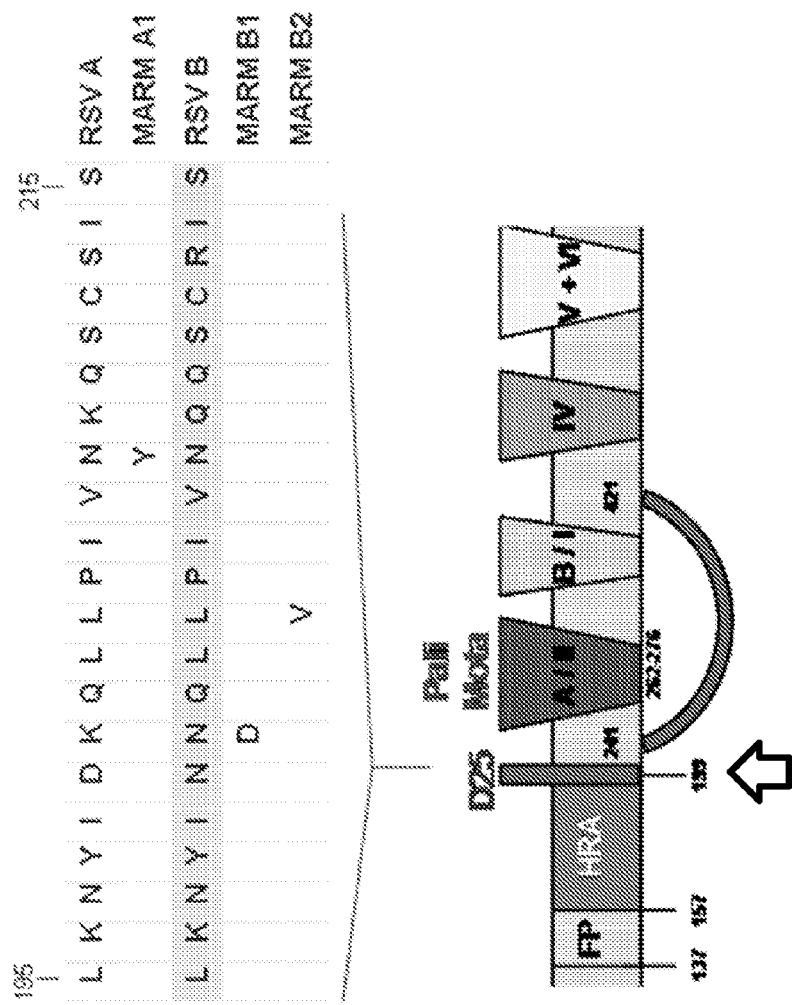

FIG. 10 shows the mapping of D25 epitope on RSV-F protein. FIG. 10A is a diagram showing the location of the 3 amino acid mutations in the identified D25 monoclonal antibody resistant mutants (MARMs). FIG. 10B is a space-filling model showing the location of the identified D25 epitope on the surface of the RSV-F protein. The bold white arrow indicates the identified epitope region critical for D25 binding.

FIG. 11 shows neutralization assays comparing the activities of D25 and motavizumab ("mota") monoclonal antibodies on the D25 MARMs.

FIG. 12 shows cell-based neutralization assays with cells infected with D25 MARMs by palivizumab and D25 monoclonal antibodies.

FIG. 13 is a diagram illustrating the construction of the SK-epitope. The underlined sequence corresponds to amino acids 195-211 of RSV A2 F protein, and the double underlined sequence corresponds to amino acids 212-228 of RSV A2 F protein, with a C212S substitution.

FIG. 14 shows the comparison of D25 binding to either the HR1 region or the SK-epitope of RSV A2 F protein, analyzed by Biolayer Interferometry.

DETAILED DESCRIPTION

DEFINITIONS

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and comprises any chain or chains of two or more amino acids. Thus, as used herein, a "peptide," a "peptide fragment," a "protein," an "amino acid chain," an "amino acid sequence," or any other term used to refer to a chain or chains of two or more amino acids, are generically included in the definition of a "polypeptide," even though each of these terms can have a more specific meaning. The term "polypeptide" can be used instead of, or interchangeably with any of these terms. The term further includes polypeptides which have undergone post-translational or post-synthesis modifications, for example, glycosylation, acetylation, phosphorylation, amidation, derivatization by known protecting/blocking groups, proteolytic cleavage, or modification by non-naturally occurring amino acids.

More specifically, the term "peptide" fragment as used herein encompasses a less-than full length peptide or a variant or derivative or analog thereof. A "peptide fragment"

as disclosed herein, e.g., an RSV-F peptide fragment, can be part of a fusion polypeptide comprising additional, non-RSV F protein components such as a surface-exposed coat protein used as a structural scaffold. A peptide as described herein can also be derivatized in a number of different ways.

The terms "analog," "derivative," or "variant" when referring to an RSV-F peptide fragment includes any peptide fragment which retains at least some desirable activity, e.g., binding to an anti-RSV antibody.

The term "variant," as used herein, refers to a peptide that differs from the recited peptide due to amino acid substitutions, deletions, insertions, and/or modifications. Variants can be produced using art-known mutagenesis techniques. Variants can also, or alternatively, contain other modifications—for example a peptide can be conjugated or coupled, e.g., fused to a heterologous amino acid sequence or other moiety, e.g., for increasing half-life, solubility, or stability. Examples of moieties to be conjugated or coupled to a peptide provided herein include, but are not limited to, albumin, an immunoglobulin Fc region, polyethylene glycol (PEG), and the like. The peptide can also be conjugated or produced coupled to a linker or other sequence for ease of synthesis, purification or identification of the peptide (e.g., 6-His), or to enhance binding of the polypeptide to a solid support.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10), and any other required parameter including but not limited to matrix option.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antigen-binding antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen-binding portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope.

The term "anti-RSV antibody" or "RSV antibody" refers to an antibody that is capable of specifically binding to an RSV virus.

The term "antibody fragment" refers to a portion of an intact antibody. Specifically, an "antigen-binding fragment" of an intact antibody is a portion of the antibody that can specifically bind an antigen. Examples of antibody fragments include, but are not limited to Fab, Fab', F(ab')2, and Fv fragments, linear antibodies, single chain antibodies, and multispecific antibodies formed from antibody fragments.

The term "epitope" refers to that portion of an antigen capable of being recognized and specifically bound by a particular antibody. When the antigen is a polypeptide, epitopes can be formed from contiguous amino acids or noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. In one specific embodiment, an epitope includes at least 6 amino acids.

A "linear epitope" or a "sequential epitope" is an epitope that is recognized by antibodies by its linear sequence of amino acids, or primary structure. A "conformational epitope" or a "nonsequential epitope" is an epitope that is recognized by antibodies by its tertiary structure. The residues that constitute these epitope may not be contiguous in the primary amino acid sequence but are brought close together in the tertiary structure of the molecule. Linear and conformational epitopes generally behave differently when a protein is denatured, fragmented, or reduced. In certain embodiments, a conformation epitope can be found on one form of a protein, e.g., the pre-fusion conformation of an RSV F protein, but not in another conformation, e.g., a post-fusion conformation of an RSV F protein. Fragmentation of a protein or reduction of its disulfide bonds often destroys conformational epitopes.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments are described in the following.

The term "immunogenic composition" as used herein refers to any pharmaceutical composition containing an RSV antigen, which composition can be used to prevent or treat an RSV infection-associated disease or condition in a subject. A preferred immunogenic composition can induce, stimulate or enhance the immune response against RSV.

The terms "composition" or "pharmaceutical composition" refer to compositions containing an isolated polypeptide provided herein, along with e.g., pharmaceutically acceptable carriers, excipients, or diluents for administration to a subject in need of treatment, e.g., a human subject infected with RSV virus.

The term "pharmaceutically acceptable" refers to compositions that are, within the scope of sound medical judgment, suitable for contact with the tissues of human beings and animals without excessive toxicity or other complications commensurate with a reasonable benefit/risk ratio.

The term "subject" is meant any subject, particularly a mammalian subject, in need of treatment with a composition comprising an isolated polypeptide provided herein. Mammalian subjects include, but are not limited to, humans, dogs, cats, guinea pigs, rabbits, rats, mice, horses, cattle, bears, cows, apes, monkeys, orangutans, and chimpanzees, and so on. In one embodiment, the subject is a human subject.

RSV F Protein

Respiratory syncytial virus (RSV) belongs to the *Pneumovirus* genus of the Paramyxoviridae family. The viral genome consists of a single-stranded RNA molecule of negative polarity that encodes 11 proteins. Two of these proteins are the major surface glycoproteins of the virion, namely: (i) the attachment protein (G) that mediates binding of the virus to the cell surface and (ii) the fusion protein (F) that promotes fusion of the virus and cell membranes during virus entry and also the fusion of the membranes of infected cells with surrounding cells to form syncytia. Two major antigenic groups, A and B, are distinguished primarily by differences in the G protein, with group A being most prevalent.

RSV-F protein is a type I glycoprotein that assembles as a homotrimer. Each monomer is synthesized as an inactive precursor (F0) that needs to be cleaved at two polybasic sites (I and II) to become fusion competent. The F protein assumes a metastable pre-fusion conformation in the virus particle until the virus binds to the target membrane. The F protein is then activated to initiate a series of conformational changes so that fusion occurs at the right time and in the right place. After fusion, F protein acquires a highly stable post-fusion conformation determined mainly by the formation of a six-helix bundle (6HB), composed of sequences of two heptad repeats (HR1 and HR2) from each monomer. The free energy released during the transition of the F protein from the pre-fusion to the post-fusion structure drives the process of membrane fusion.

The term "RSV-F protein" refers to a naturally occurring or a recombinantly made full length F protein from an RSV virus, and fragments, variants, analogs, or derivatives thereof. An RSV F protein can be in pre-fusion or post-fusion conformation. In certain embodiments, the RSV virus is a human RSV virus. In certain embodiments, the RSV virus is of the subtype A. In one specific embodiment, the RSV subtype A is RSV A2. In other embodiments, the RSV virus is of the subtype B. In one specific embodiment, the RSV subtype B is RSV 18537. In another specific embodiment, the RSV subtype B is RSV B9320.

The terms "de novo F protein" or "pre-fusion F protein" refer to an RSV-F protein in its pre-fusion conformation. It has been shown that native, untriggered RSV-F protein exists in a metastable state that can be converted in vitro to the more stable, fusogenic six-helix bundle conformation by an increase in the thermal energy, such as by heating at 55° C. to 60° C. for 10 to 15 minutes.

Representative RSV-A (strain A2) and RSV-B (strain 18537) F protein sequences are shown below. The predicted signal peptides are double underlined, and the regions identified to contain the epitope for mAb D25 is single underlined.

```
RSV-A F protein sequence from strain A2
                                                         (SEQ ID NO: 1)
>gi|2627305|gb|AAB86664.1| fusion F glycoprotein precursor [Human
respiratory syncytial virus]
   1 MELLILKANA ITTILTAVTF CFASGQNITE EFYQSTCSAV SKGYLSALRT GWYTSVITIE

61 LSNIKENKCN GTDAKVKLIK QELDKYKNAV TELQLLMQST PATNNRARRE LPRFMNYTLN

121 NAKKTNVTLS KKRKRRFLGF LLGVGSAIAS GVAVSKVLHL EGEVNKIKSA LLSTNKAVVS

181 LSNGVSVLTS KVLDLKNYID KQLLPIVNKQ SCSISNIATV IEFQQKNNRL LEITREFSVN

241 AGVTTPVSTY MLTNSELLSL INDMPITNDQ KKLMSNNVQI VRQQSYSIMS IIKEEVLAYV

301 VQLPLYGVID TPCWKLHTSP LCTTNTKEGS NICLTRTDRG WYCDNAGSVS FFPQAETCKV

361 QSNRVFCDTM NSLTLPSEVN LCNVDIFNPK YDCKIMTSKT DVSSSVITSL GAIVSCYGKT

421 KCTASNKNRG IIKTFSNGCD YVSNKGVDTV SVGNTLYYVN KQEGKSLYVK GEPIINFYDP

481 LVFPSDEFDA SISQVNEKIN QSLAFIRKSD ELLHNVNAGK STINIMITTI IIVIIVILLS

541 LIAVGLLLYC KARSTPVTLS KDQLSGINNI AFSN
```

-continued

RSV-B F protein sequence from strain 18537
(SEQ ID NO: 2)
>gi|222565|dbj|BAA00240.1| fusion protein precursor [Human respiratory syncytial virus]

```
  1 MELLIHRSSA IFLTLAVNAL YLTSSQNITE EFYQSTCSAV SRGYFSALRT GWYTSVITIE

61 LSNIKETKCN GTDTKVKLIK QELDKYKNAV TELQLLMQNT PAANNRARRE APQYMNYTIN

121 TTKNLNVSIS KKRKRRFLGF LLGVGSAIAS GIAVSKVLHL EGEVNKIKNA LLSTNKAVVS

181 LSNGVSVLTS KVLDLKNYIN NRLLPIVNQQ SCRISNIETV IEFQQMNSRL LEITREFSVN

241 AGVTTPLSTY MLTNSELLSL INDMPITNDQ KKLMSSNVQI VRQQSYSIMS IIKEEVLAYV

301 VQLPIYGVID TPCWKLHTSP LCTTNIKEGS NICLTRTDRG WYCDNAGSVS FFPQADTCKV

361 QSNRVFCDTM NSLTLPSEVS LCNTDIFNSK YDCKIMTSKT DISSSVITSL GAIVSCYGKT

421 KCTASNKNRG IIKTFSNGCD YVSNKGVDTV SVGNTLYYVN KLEGKNLYVK GEPIINYYDP

481 LVFPSDEFDA SISQVNEKIN QSLAFIRRSD ELLHNVNTGK STTNIMITTI IIVIIVVLLS

541 LIAIGLLLYC KAKNTPVTLS KDQLSGINNI AFSK
```

Anti-RSV Antibody D25

The terms "monoclonal antibody D25" or "mAb D25," refers to the anti-RSV monoclonal antibody designated "D25," as well as an antigen-binding fragment, variant, derivative and/or analog thereof, as previously described in WO 2008/147196, which is incorporated herein by reference in its entirety.

Also included are fragments, derivatives, analogs, or variants of a D25 mAb, and any combination thereof. The terms "fragment," "variant," "derivative," and "analog" when referring to D25 mAb refers to any polypeptides that retain at least some of the antigen-binding properties of the corresponding antibody or antibody polypeptide of the invention. Fragments include proteolytic fragments, as well as deletion fragments, in addition to specific antibody fragments discussed elsewhere herein. Variants of D25 mAbs include fragments as described above, and also polypeptides with altered amino acid sequences due to amino acid substitutions, deletions, or insertions. Variants can occur naturally or be non-naturally occurring. Variant antibodies can comprise conservative or non-conservative amino acid substitutions, deletions, or additions. As used herein a "derivative" of a D25 mAb refers to an antibody or fragment thereof having one or more residues chemically derivatized by reaction of a functional side group. An analog of a D25 mAb possesses analogous properties. This is for instance done through screening of a peptide library or phage display library for D25 analogs that bind to the conformational epitope provided herein.

RSV-F Protein Epitopes

As demonstrated in the Examples, mAb D25 binds to a conformational epitope on the pre-fusion form of RSV F protein. D25 does not bind abundantly to soluble F protein. D25 binds to the surface of unfixed RSV-infected cells, but does not bind to fixed infected cells. In addition, D25 does not bind to the surface of infected cells that have been heated, an in vitro treatment that induces RSV F protein to assume the post-fusion conformation.

This disclosure provides a conformational epitope on the surface of a respiratory syncytial virus fusion (RSV F) protein, comprising at least 6 amino acids within amino acids 1 to 34 of SEQ ID NO:7 (i.e., amino acids 195 to 228 of SEQ ID NO:1) or amino acids 1 to 34 of SEQ ID NO:9 (i.e., amino acids 195 to 228 of SEQ ID NO:2). As provided herein, an RSV F protein comprising the epitope can be specifically bound by monoclonal antibody D25 or an antigen-binding fragment, analog, variant, or derivative thereof, provided that the RSV F protein is in pre-fusion conformation.

In certain embodiments, an RSV F protein in pre-fusion conformation comprising a conformational epitope as provided herein can be bound by monoclonal antibody D25, or a fragment, variant, analog, or derivative thereof with at least 100-fold greater affinity than an RSV F protein comprising the amino acid sequence of SEQ ID NO:12, SEQ ID NO:13, or SEQ ID NO:14 (MARM mutants).

A conformational epitope as provided herein can be located on the surface of a human RSV subtype A F protein, e.g., from RSV strain A2 or a human RSV subtype B F protein, e.g., from RSV strain 18537.

Also provided is an isolated structure comprising a conformation epitope as provided herein and as described above, where the epitope is specifically bound to monoclonal antibody D25 or an antigen-binding fragment, variant, analog, or derivative thereof. In certain embodiments the structure is a crystal structure.

Also provided is an isolated fusion protein comprising a conformational epitope as provided herein. In certain embodiments, the fusion protein includes an RSV F protein fragment comprising, consisting of, or consisting essentially of amino acids 1 to 34 of SEQ ID NO:7 or amino acids 1 to 34 of SEQ ID NO:9; and a polypeptide scaffold. In certain embodiments, the fusion protein is constrained in a conformation that can be specifically bound by monoclonal antibody D25 or an antigen-binding fragment, variant, analog, or derivative thereof. In certain embodiments, the scaffold can comprise a surface-exposed coat protein. In some embodiments, the surface-exposed coat protein is a protease inhibitor, such as one in the Kunitz family or the squash family of protease inhibitors. In certain embodiments, the scaffold protein is the *Ecballium elaterium* trypsin inhibitor II (EETI-II). Christmann, et al. Protein Eng. 12:797-806 (1999). In certain embodiments, the inhibitor loop of EETI-II is replaced by amino acids 1 to 34 of SEQ ID NO:7 or amino acids 1 to 34 of SEQ ID NO:9. In certain embodiments, the fusion protein comprises the amino acid sequence of SEQ ID NO: 5.

Any of the polypeptides provided herein can be part of a fusion peptide, wherein the RSV-F epitope is conformationally constrained in a structural scaffold. The fusion peptide may or may not comprise linker sequences. In some embodiments, the epitope is fused to a surface-exposed coat protein.

In one embodiment, the inhibitor loop of EETI-II (corresponding to residues 3-8) is replaced by residues 195-228 of SEQ ID NO:1 or SEQ ID NO:2. In a more specific embodiment, the cysteine at position 212 of the RSV-F protein is substituted.

Also provide is an isolated polynucleotide which encodes any fusion protein as described above. Further provided is a vector, e.g., an expression vector comprising the polynucleotide, and a host cell comprising the polynucleotide or the vector.

Also provided is a recombinant RSV antigen comprising a fusion peptide as described herein. In certain embodiments a fusion protein as provided herein can be formulated as an immunogenic composition which, when administered to a subject in need thereof, can elicit an immune response against RSV. In certain embodiments, an immunogenic composition comprises one or more of a carrier, an excipient, or an adjuvant.

Compositions of the disclosure can be formulated according to known methods. Suitable preparation methods are described, for example, in Remington's Pharmaceutical Sciences, 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, the compositions as provided herein can be administered directly to the subject.

Carriers that can be used with the compositions provided herein are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

In certain embodiments, a fusion protein as provided herein can be used in a method for identifying anti-RSV F protein antibodies which bind to the same conformational epitope as described herein, and are thus analogous to the D25 mAb. For example, the fusion protein can be used to screen an antibody library for antibodies that bind to the fusion protein, but do not bind to the scaffold protein alone. Antibody libraries and methods of panning and/or screening for antibodies which specifically bind to a particular antigen are well known to persons of ordinary skill in the art.

Some RSV-F epitope sequences used in the embodiments are listed in Table 1 below.

TABLE 1

Heptad Repeat sequences for RSV-F protein constructs

1A. HR1xHR2
(SEQ ID NO: 3)
containing amino acids 153-221 (bold) and amino acids 476-520 (italicized) of RSV A2 F protein.
MghhhhhhhhhhssghiddddkhMAVSKVLHLEGEVNKIKSALLSTNKAVVSLSNGVSVLTSKVLDLKNYIDKQLLPIVNK
QSGGSGKGGTGGGSGKNFYDPLVFPSDEFDASISQVNEKINQSLAFIRKSDELLHNVNAGK 1B. HR1
(SEQ ID NO: 4)
containing amino acids 153-221 (bold) of RSV A2 F protein.
MghhhhhhhhhhssghiddddkhMAVSKVLHLEGEVNKIKSALLSTNKAVVSLSNGVSVLTSKVLDLKNYIDKQLLPIVNK
QS 1C. SK-Epitope - containing amino acids 195-211 (bold and underlined) of RSV A2 F
protein HR1 region and the subsequent amino acids 212-228 (double-underlined,
with C212S mutation) of RSV F protein, which replaces the inhibitor loop of
EETI-II (FIG. 8).
(SEQ ID NO: 5)
QPAMAMDIGINSDPGCEFLKNYIDKQLLPIVNKQSSSISNIATVIEFQQKNNLQCKQDSDCLAGCVCGPNGFCGVDKLAA (SEQ ID NO: 6)
ALEHHHHHH (linker and his tag to be fused to SEQ ID NO:5)

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1

D25 Binds to Cells Expressing the Pre-Fusion Form of RSV-F Protein

In an effort to understand the requirements for binding to the neutralization epitope recognized by the antibody D25, a number of strategies were employed.

First, an ELISA assay was carried out to test the binding of D25 to acetone fixed or unfixed HEp-2 cells infected with an RSV-A2 virus (ATCC VR-1540), in order to determine whether D25 binds to the pre-fusion or the post-fusion conformation of the RSV-F protein. The binding of other two anti-RSV-F protein monoclonal antibodies, palivizumab and motavizumab, was also tested. R347 was used as a negative control for the binding.

HEp2 (ATCC CCL-23) were grown to 90% confluence in EMEM medium plus 5% FBS in a 96 well plate. Cells were infected with a multiplicity of infection of 0.5-1.0 (assuming a total cell number per well of ~5×10$^4$) of RSV A2 virus (ATCC VR-1540). After infection for 24 hours, the medium was removed and the cells were fixed to the plate by drying (unfixed) or by treatment for 20 minutes with 80% acetone then dried. Infected cell layers were blocked with 1% casein block (Thermo) for 1 hour prior to incubation with antibody diluted in casein ranging from 1000 ng/ml to 1 ng/ml. Antibody was incubated for 1 hour at room temperature, washed with PBS/0.1% Tween-20 and incubated with 1:10000 dilution of anti-human HRP conjugate antibody (Jackson Immuno-research) for 1 hour at room temperature. Plates were washed and developed using SureBlue Reserve reagent (KPL). Absorbance was measured at 450 nm.

Figure 1:
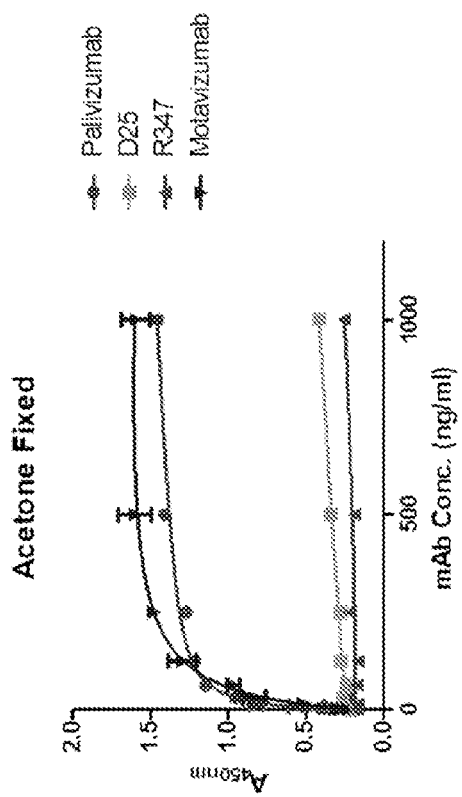
FIG. 1 shows the binding of D25 monoclonal antibody to unfixed and acetone fixed HEp-2 cells infected with RSV A2 virus (ATCC VR-1540), in comparison with the binding of palivizumab, motavizumab, and R347 (as negative control).
Figure 1:
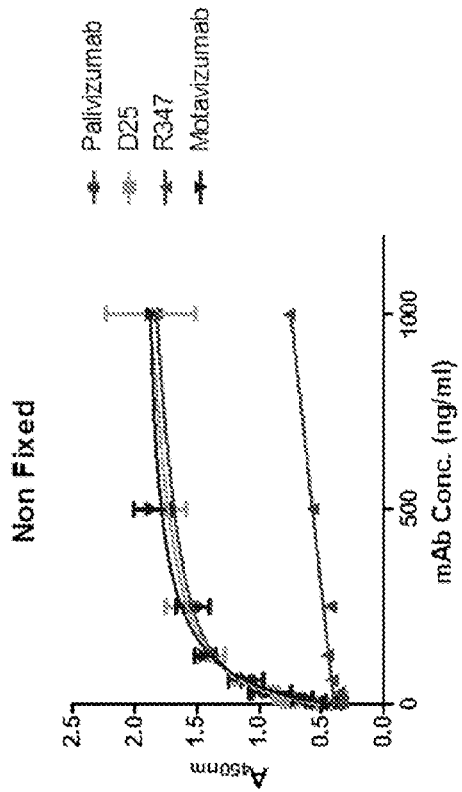

As shown in FIG. 1A, D25 bound to unfixed RSV-A2 infected HEp-2 cells in a concentration-dependent manner, but showed little binding to the acetone fixed RSV-A2 infected HEp-2 cells (FIG. 1B), while palivizumab and motavizumab bound to both fixed and unfixed cells in similar manners.

Example 2

D25 does not Bind to Heat-Treated RSV-F Protein

To confirm that D25 only recognizes a conformational epitope on pre-fusion RSV-F protein, the binding of Eu$^{3+}$-labeled D25 was tested on unheated de novo RSV-F protein which represents the pre-fusion form, or heated (flipped) RSV-F protein which resembles the post-fusion form.

A stably transfected 293 line expressing RSV A2 F protein sequence under the tetracycline inducible promoter (TREx-F cells) has been previously described in Huang, K. et. al., Virus Genes 40:212-221 (2010), which is incorporated herein by reference in its entirety. Motavizumab, D25, and R347 (as negative control) were Eu$^{3+}$-labeled using the Delfia Eu-N1-ITC labeling chelate and were characterized according to the manufacturer's directions (Perkin Elmer). TREx-F cells were grown to confluence and F protein expression was induced with tetracycline at 15 µg/ml for 20 h post induction. Cells were then collected and resuspended to ~1×10$^7$ viable cells/ml in 50% media/50% LR Binding Buffer (Tris based buffer system, Perkin Elmer). Cells were either kept on ice or treated in a water bath of 15 minutes at 55° C. Approximately 1×10$^5$ cells were mixed with 25 nM Eu$^{3+}$ labeled motavizumab, D25 or R347 in LR Binding Buffer in a 100-µl reaction volume. The cells plus monoclonal antibody were incubated for 1 h at 4° C., and then added to Pall GHP vacuum filter plates. Unbound monoclonal antibody was washed away with 5×200 µl washes with Delfia Assay Wash Buffer (Perkin Elmer), and Eu$^{3+}$ fluorescence was released with the addition of 200 µl Enhancement Solution (Perkin Elmer). Time Resolved Fluorescence was read on an Envision Reader (Perkin Elmer) after 1 h incubation at 37° C. with gentle shaking. Eu$^{3+}$ counts were converted to bound ng IgG, and specific bound motavizumab or D25 calculated by subtracting R347 nonspecific binding from total bound.

Figure 2:
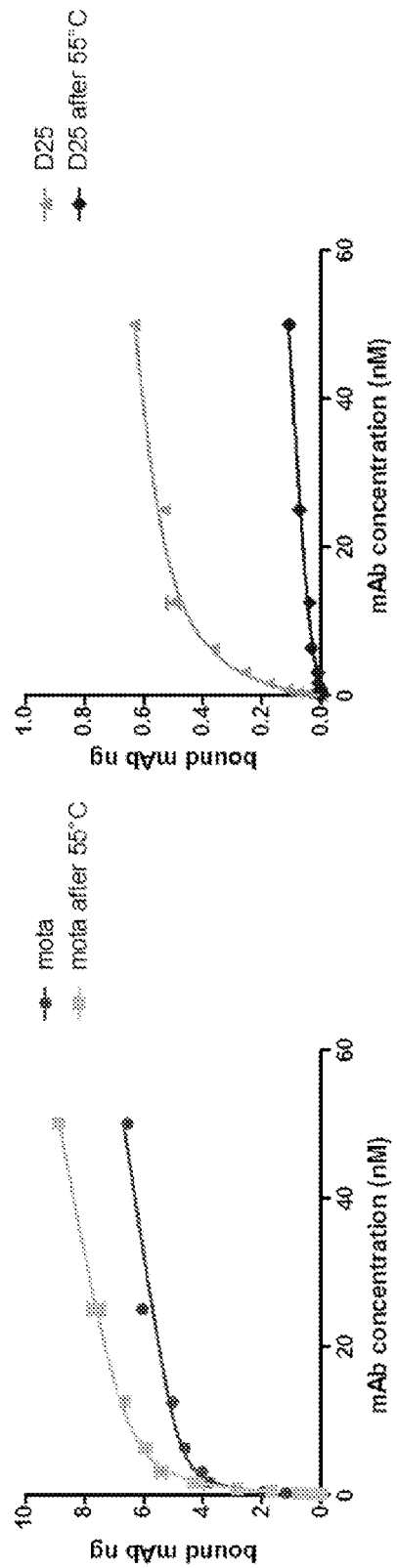
FIG. 2 shows the binding of $Eu^{3+}$-labeled motavizumab ("mota") and D25 to de novo or heat-treated RSV-F protein. 293 cells stably transfected with RSV A2 F protein were either kept on ice or treated in a water bath for 15 minutes at 55° C.

As shown in FIG. 2, heating of the RSV-F expressing 293 cells at 55° C. for 15 min almost completely abolished the binding of D25 to the cells (FIG. 2B), while only slightly decreased the binding of motavizumab (FIG. 2A). Therefore, this cell binding assay result confirms that D25 reacts to a conformational epitope that only exists in the pre-fusion form of the RSV-F protein.

Example 3

D25 Binding Studies by Biolayer Interometry Analysis

Biolayer Interometry Analysis was used to determine the effect of RSV-F protein conformational change by heating or long-term storage at 4° C. on the binding of D25 to RSV-F protein.

Figure 3:
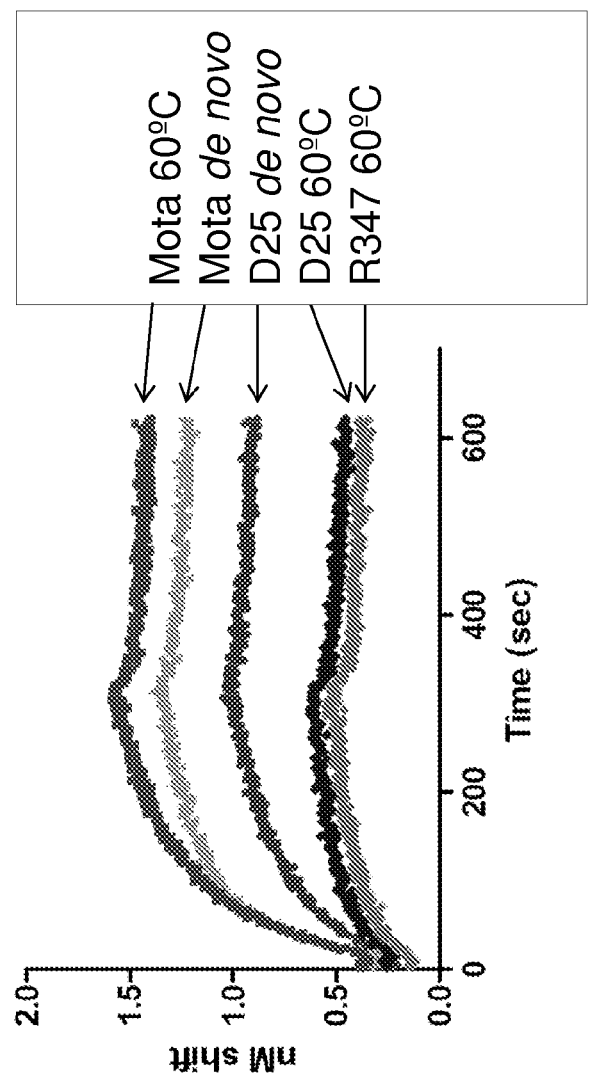
FIG. 3 shows the Biolayer Interferometry Analysis (FIG. 3A) to test the binding of motavizumab ("mota") and D25 to de novo or heat-treated RSV-F protein (FIG. 3B). R347 was used as negative control.
Figure 3:
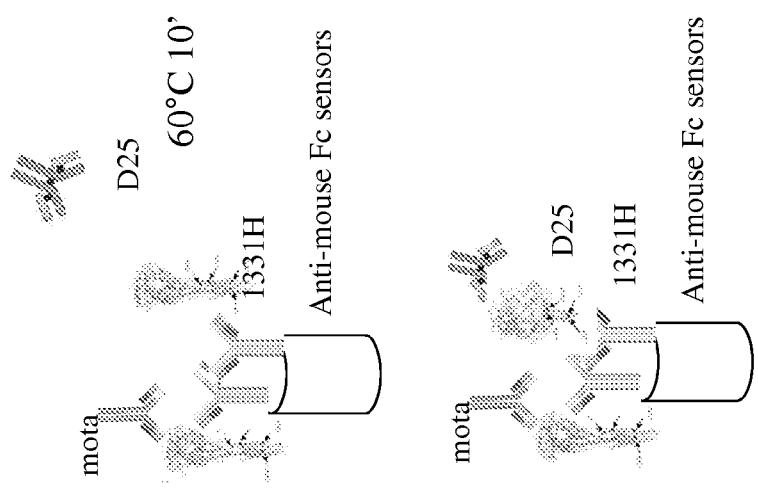

As illustrated in FIG. 3A, to test the effect of heating, monoclonal antibody 1331H, which reacts to the defined C site of RSV F protein (Yunus et al., Virology, 396(2): 226-237 (2010); Beeler and Coelingh, Journal of Virology, 63(7): 2941-2950 (1989)), was bound to an anti-mouse Fc capture sensor (ForteBio). Sensors were first incubated with RSV-F protein that was either heated to 60° C. for 10 min or unheated (de novo), then moved to the wells containing motavizumab, R347 (negative control). Binding of antibody to the sensor+1331H+sF complex was detected as deflection of the signal read as a change in the nm of light ($\Delta$ nm).

As shown in FIG. 3B, consistent with the cell-binding results in Example 2, D25 binding to RSV-F protein was almost completely abolished when the F protein was heated, while motavizumab bound to both de novo and heated RSV-F proteins.

Similarly, to test the effect of long-term storage at 4° C., the sensor+1331H complex was first incubated with RSV-F protein that was either stored at 4° C. in CD CHO medium for 6 to 7 weeks or without storage, then moved to the wells containing D25 or Motavisumab, and $\Delta$ nm was measured.

Figure 4:
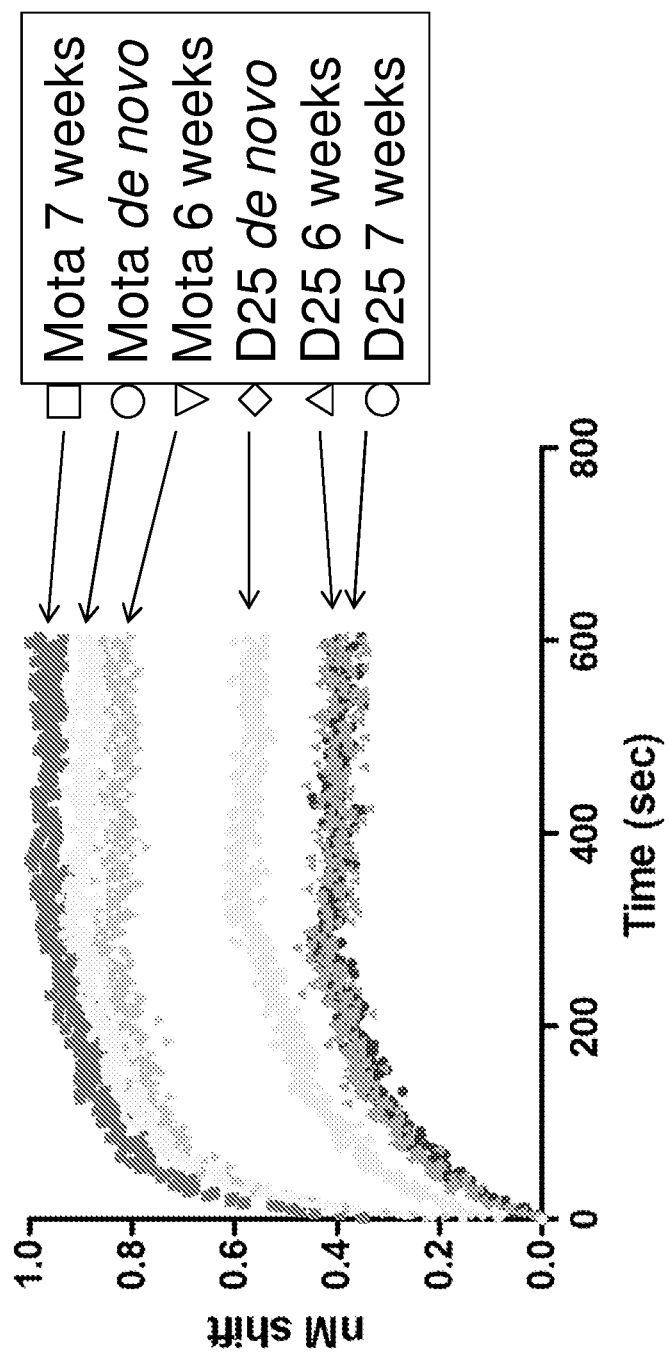
FIG. 4 shows the slow loss of binding of D25 to RSV-F protein after storage at 4° C., in comparison with the binding of motavizumab ("mota") to RSV-F protein under same conditions, as analyzed by Biolayer Interferometry.

FIG. 4 shows that there was a slow loss of binding of D25 to RSV-F protein when stored at 4° C. in CD CHO medium, probably due to conformational change of the F protein. In contrast, motavizumab showed no loss of binding after storage for 7 weeks at 4° C., consistent with the finding that it recognizes a nonconformational epitope.

Taken together, these Biolayer Interometry Analysis experiments further confirm that D25 reacts to a conformational epitope that exists in the pre-fusion form of the RSV-F protein.

Example 4

D25 does not Compete with Anti-6-Helix Bundle Antibody

Biolayer Interometry Analysis was used to further determine the location of the D25 epitope, in particular, to test whether D25 competes with other RSV antibodies with well-characterized epitope regions.

Figure 5:
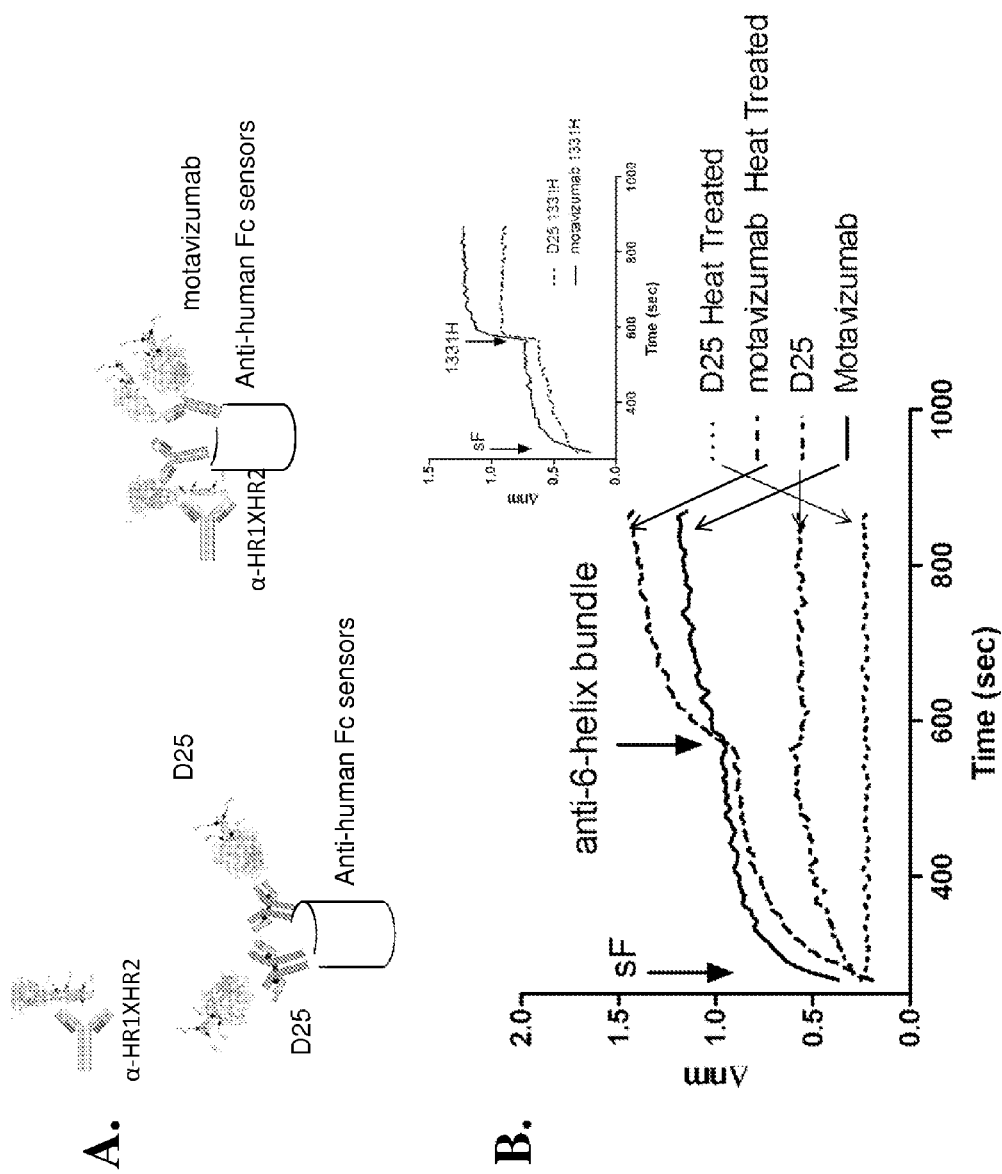
FIG. 5 shows the Biolayer Interferometry Analysis to test the binding of motavizumab and D25 to de novo or heat-treated RSV-F protein, followed by subsequent binding to either a rabbit anti-6-helix bundle polyclonal antibody (FIG. 5B) or an anti-RSV-F C site monoclonal antibody 1331H (FIG. 5B insert). Motavizumab and D25 were immobilized to an anti-human IgG Fc capture sensor (FIG. 5A).

As illustrated in FIG. 5A, D25, motavizumab, or negative control antibody R347 was bound to an anti-human IgG Fc capture sensor (ForteBio) at a concentration of 1.5 μg/ml. Sensors were moved to a well containing kinetics buffer (ForteBio) to establish a baseline prior to moving to a well containing either sF containing CHO medium that was either heated to 60° C. for 10 minutes or untreated. Sensors were moved to the next well containing either 30 μg/ml of affinity purified rabbit polyclonal IgG reactive to the six helix bundle of the post-fusion form of RSV F protein or to 15 μg/ml of mAb 1331H, an antibody that reacts to the defined C site of RSV F protein (Yunus et al., Virology, 396(2): 226-237 (2010); Beeler and Coelingh, Journal of Virology, 63(7): 2941-2950 (1989)). All binding curves were baseline subtracted relative to the negative control antibody. Binding of protein to the sensor is detected as deflection of the signal read as a change in the nm of light ($\Delta$ nm).

The results shown in FIG. 5B confirm that D25 bound to unheated (pre-fusion) RSV-F protein, but not to heat-treated (post-fusion) F protein which had strong binding to the rabbit anti-6-helix bundle (6×HB) antibody. The insert in FIG. 5B shows that D25 and 1331H recognize different epitopes on the pre-fusion form of RSV-F protein.

Example 5

D25 does not Compete with Antibodies Binding to Antigenic Sites A, B, or C

Figure 6:
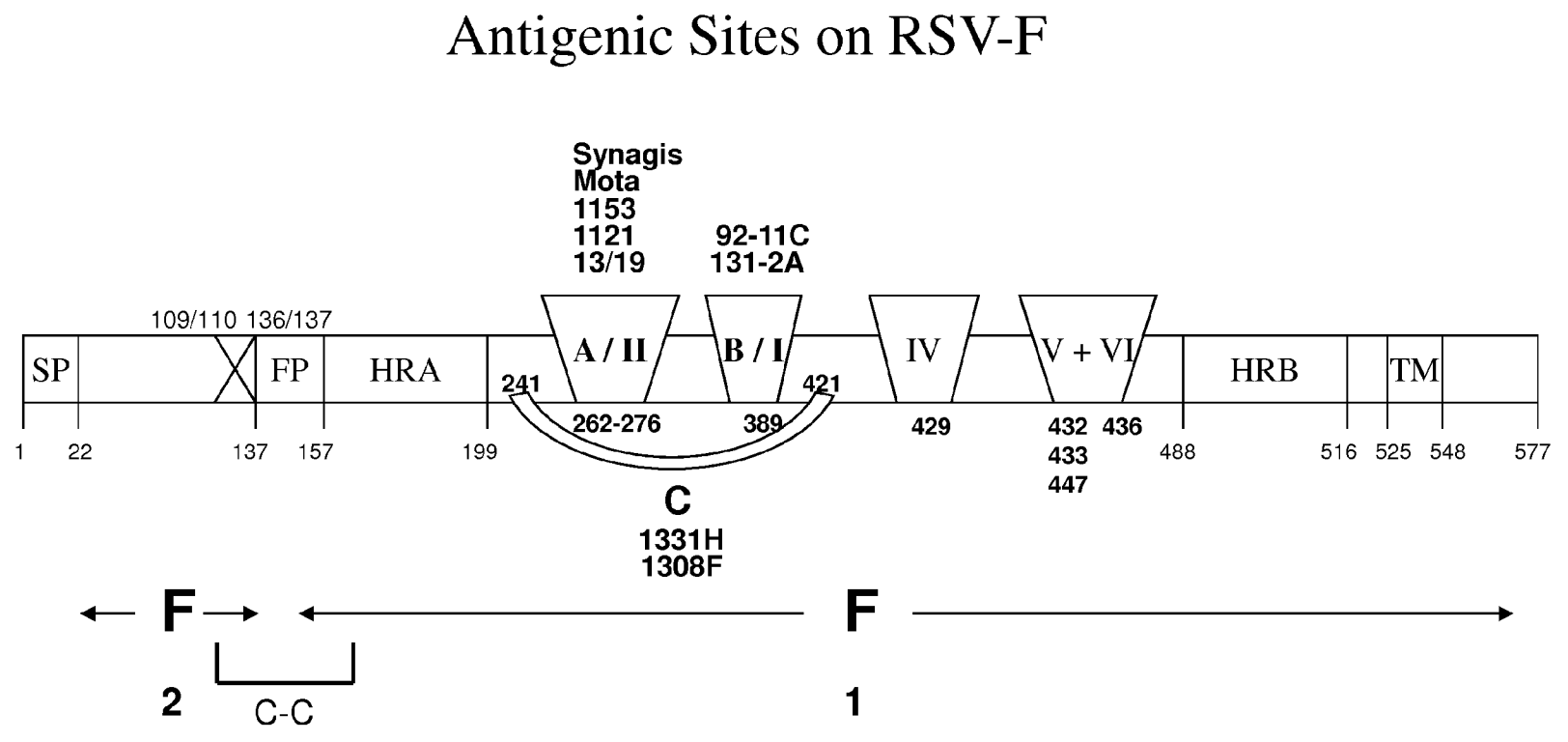

RSV-F protein has at least 6 different commonly described neutralizing antigenic sites. Previously identified anti-RSV monoclonal antibodies, palivizumab (SYNAGIS®), motavizumab, 1153, 1121, 13/19, 92-11C, 131-2A, 1331H, and 1308F, bind to well characterized antigenic sites A/II, B/I, or C, as illustrated in FIG. 6.

In order to determine whether D25 binds to any one of these well-characterized antigenic regions, competitive binding assays were carried out to test whether any of the aforementioned anti-RSV antibodies can compete with D25 for its antigenic site. 100 ng/ml biotin-labeled D25 antibody was used in all the binding assays. Unlabeled D25 was used as positive control and R347 was used as negative control. Absorbance was measured at 450 nm.

Figure 7:
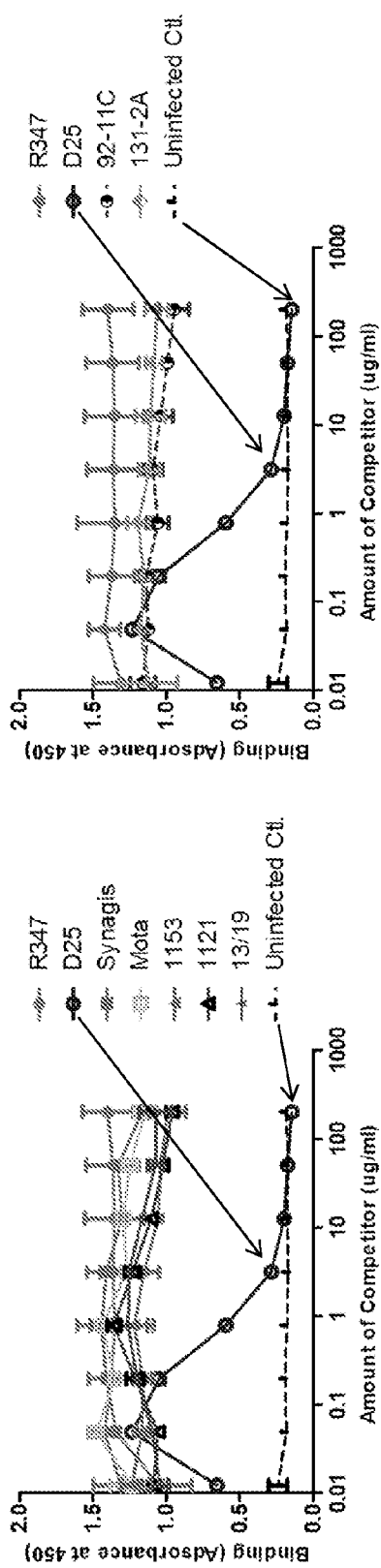
FIG. 7 shows the competition binding assay using various anti-RSV-F antibodies with known antigenic sites to identify D25 epitope. 100 ng/ml biotin-labeled D25 antibody was used for all the binding assays.
Figure 7:
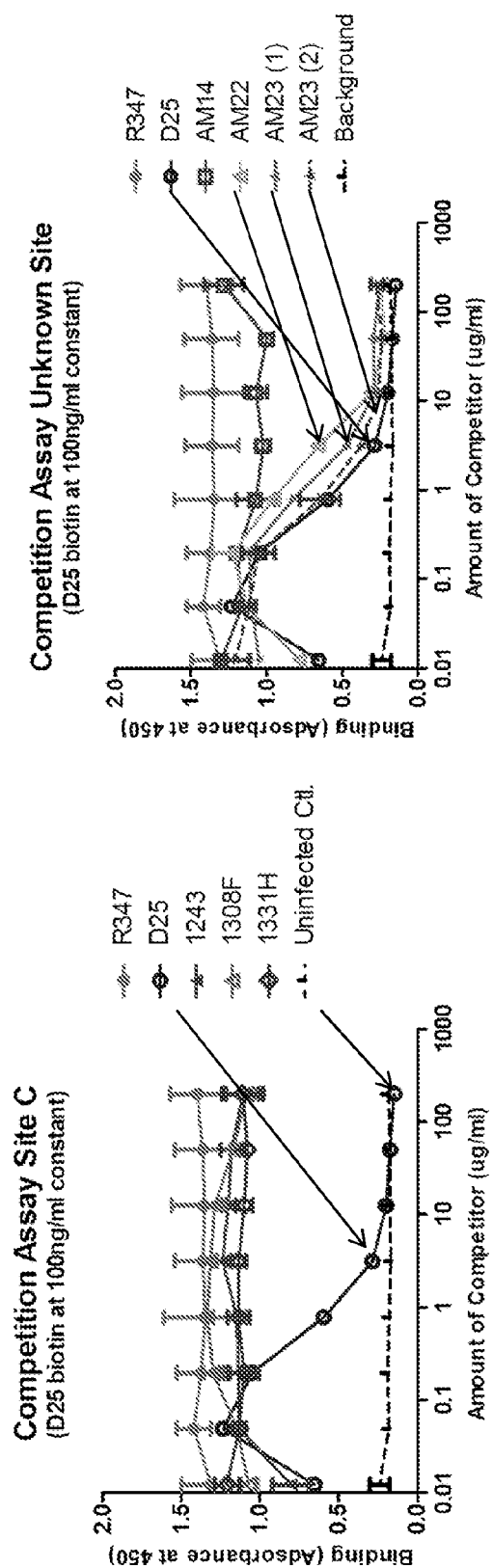

As shown in FIGS. 7A-C, none of the antibodies known to bind to antigenic site A, B, or C were able to compete with D25 for its binding to RSV-F protein, indicating that D25 does not bind to site A, B, or C. On the other hand, as shown in FIG. 7D, a few anti-RSV-F antibodies with unknown antigenic site, namely, AM22 and AM23, effectively competed with D25 in the binding assay, suggesting that D25's epitope overlaps with those of AM22 and AM23. AM23 competed with D25 more effectively than AM22, suggesting that its epitope may be more similar to that of D25.

AM22 and AM23 were previously disclosed in US 2012/0070446 A1 and US 2010/0239593 A1, respectively. It was previously found that AM23 did not neutralize any of the RSV B strains except for one clinical isolate (CP096-B15). It was also shown that amino acid 209 was important for AM23's neutralization activity (FIG. 8). Taken together, these results suggest that D25 may bind to an antigenic region including amino acid 209.

Example 6

Mapping of the D25 Epitope

This example reports the generation of a series of monoclonal antibody resistant mutants (MARMs) that cannot be neutralized by D25, to further determine which amino acids of the RSF-F protein are critical for D25 binding.

This analysis was performed on an A isolate and a B isolate of the RSV virus.

Briefly, 1-5×10⁶ pfu/ml of RSV A2 or RSV B 18537 viruses were incubated in 450 ng/ml (200×IC$_{50}$) D25 mAb for 1 hour prior to infection of confluent HEp2 cells in a 24 well plate. Up to 6 days post infection the plates were frozen and thawed to release the virus and supernatants from this process were passaged on a new confluent layer of Hep2 cells following a 2 hour incubation with 450 ng/ml of D25.

A third passage was performed as described for the second passage. Virus yield following 3 rounds of selection was 8×10⁵ to 3×10⁶ for A2 virus and 1.3×10⁴ to 5×10⁴ for the B virus. Following the third passage, cells were retained, lysed and total RNA isolated from the cells. The F protein gene was amplified by PCR and sequenced.

The mutant F proteins for RSV MARMs A1, B1 and B2 are shown below and in FIG. 10A. The signal peptide is double-underlined, the region comprising the conformational epitope in the wild-type RSV F A2 protein is underlined. The mutant amino acid for each mutant is shown in BOLD.

```
MARM A1 F Protein Sequence
                                                         (SEQ ID NO: 12)
  1 MELLILKANA ITTILTAVTF CFASGQNITE EFYQSTCSAV SKGYLSALRT GWYTSVITIE

61 LSNIKENKCN GTDAKVKLIK QELDKYKNAV TELQLLMQST PATNNRARRE LPRFMNYTLN

121 NAKKTNVTLS KKRKRRFLGF LLGVGSAIAS GVAVSKVLHL EGEVNKIKSA LLSTNKAVVS

181 LSNGVSVLTS KVLDLKNYID KQLLPIVYKQ SCSISNIATV IEFQQKNNRL LEITREFSVN

241 AGVTTPVSTY MLTNSELLSL INDMPITNDQ KKLMSNNVQI VRQQSYSIMS IIKEEVLAYV

301 VQLPLYGVID TPCWKLHTSP LCTTNTKEGS NICLTRTDRG WYCDNAGSVS FFPQAETCKV

361 QSNRVFCDTM NSLTLPSEVN LCNVDIFNPK YDCKIMTSKT DVSSSVITSL GAIVSCYGKT

421 KCTASNKNRG IIKTFSNGCD YVSNKGVDTV SVGNTLYYVN KQEGKSLYVK GEPIINFYDP

481 LVFPSDEFDA SISQVNEKIN QSLAFIRKSD ELLHNVNAGK STINIMITTI IIVIIVILLS

541 LIAVGLLLYC KARSTPVTLS KDQLSGINNI AFSN

MARM B1 F Protein Sequence
                                                         (SEQ ID NO: 13)
  1 MELLIHRSSA IFLTLAVNAL YLTSSQNITE EFYQSTCSAV SRGYFSALRT GWYTSVITIE

61 LSNIKETKCN GTDTKVKLIK QELDKYKNAV TELQLLMQNT PAANNRARRE APQYMNYTIN

121 TTKNLNVSIS KKRKRRFLGF LLGVGSAIAS GIAVSKVLHL EGEVNKIKNA LLSTNKAVVS

181 LSNGVSVLTS KVLDLKNYIN DRLLPIVNQQ SCRISNIETV IEFQQMNSRL LEITREFSVN

241 AGVTTPLSTY MLTNSELLSL INDMPITNDQ KKLMSSNVQI VRQQSYSIMS IIKEEVLAYV

301 VQLPIYGVID TPCWKLHTSP LCTTNIKEGS NICLTRTDRG WYCDNAGSVS FFPQADTCKV

361 QSNRVFCDTM NSLTLPSEVS LCNTDIFNSK YDCKIMTSKT DISSSVITSL GAIVSCYGKT

421 KCTASNKNRG IIKTFSNGCD YVSNKGVDTV SVGNTLYYVN KLEGKNLYVK GEPIINYYDP

481 LVFPSDEFDA SISQVNEKIN QSLAFIRRSD ELLHNVNTGK STTNIMITTI IIVIIVVLLS

541 LIAIGLLLYC KAKNTPVTLS KDQLSGINNI AFSK

MARM B2 F Protein Sequence
                                                         (SEQ ID NO: 14)
  1 MELLIHRSSA IFLTLAVNAL YLTSSQNITE EFYQSTCSAV SRGYFSALRT GWYTSVITIE

61 LSNIKETKCN GTDTKVKLIK QELDKYKNAV TELQLLMQNT PAANNRARRE APQYMNYTIN

121 TTKNLNVSIS KKRKRRFLGF LLGVGSAIAS GIAVSKVLHL EGEVNKIKNA LLSTNKAVVS

181 LSNGVSVLTS KVLDLKNYIN NRLVPIVNQQ SCRISNIETV IEFQQMNSRL LEITREFSVN

241 AGVTTPLSTY MLTNSELLSL INDMPITNDQ KKLMSSNVQI VRQQSYSIMS IIKEEVLAYV

301 VQLPIYGVID TPCWKLHTSP LCTTNIKEGS NICLTRTDRG WYCDNAGSVS FFPQADTCKV

361 QSNRVFCDTM NSLTLPSEVS LCNTDIFNSK YDCKIMTSKT DISSSVITSL GAIVSCYGKT

421 KCTASNKNRG IIKTFSNGCD YVSNKGVDTV SVGNTLYYVN KLEGKNLYVK GEPIINYYDP

481 LVFPSDEFDA SISQVNEKIN QSLAFIRRSD ELLHNVNTGK STTNIMITTI IIVIIVVLLS

541 LIAIGLLLYC KAKNTPVTLS KDQLSGINNI AFSK
```

Eight D25 MARMS (RSV MARMs A1-A5 and B1-B3) were isolated. MARMs A1-A5 were found to have the same mutations (FIG. 9). MARMs B2 and B3 were found to have the same mutations (FIG. 9).

The mutations were located at amino acid N208Y for the MARM A1 mutant virus, amino acid N201D in the MARM B1 mutant virus, and amino acid L204V in the MARM B2 virus. This region (underlined in the sequences above) is C-terminal to the defined heptad repeats of the F protein that are critical for the fusion process of the protein. This identified D25 epitope region (indicated by a bold white arrow in FIG. 10B) is on the surface of the RSV-F protein.

The sequences are compared in Table 2 below:

TABLE 2

D25 MARM sequences in comparison with wild type RSV-F protein sequences (the mutated residues are in bold and underlined)

| Peptide | Sequence | SEQ ID NO: |
|---|---|---|
| RSV-F Wild-type A (195-228) | LKNYI DKQLL PIVNK QSCSI SNIET VIEFQ QKNN | 7 |
| RSV-F D25 MARM A1 (195-228) | LKNYI DKQLL PIVYK QSCSI SNIET VIEFQ QKNN | 8 |
| RSV-F Wild-type B (195-228) | LKNYI NNRLL PIVNQ QSCRI SNIET VIEFQ QMNS | 9 |
| RSV-F D25 MARM B1 (195-228) | LKNYI NDRLL PIVNQ QSCRI SNIET VIEFQ QMNS | 10 |
| RSV-F D25 MARM B2 (195-228) | LKNYI NNRLV PIVNQ QSCRI SNIET VIEFQ QMNS | 11 |

Example 7

Neutralization Assay of the D25 MARMs

An RSV microneutralization assay was carried out to test the isolated D25 MARMs. It was a cell based ELISA assay where infected HEp-2 cells were stained for expression of the wild type or mutated F proteins and tested for antibody binding.

Figure 11:
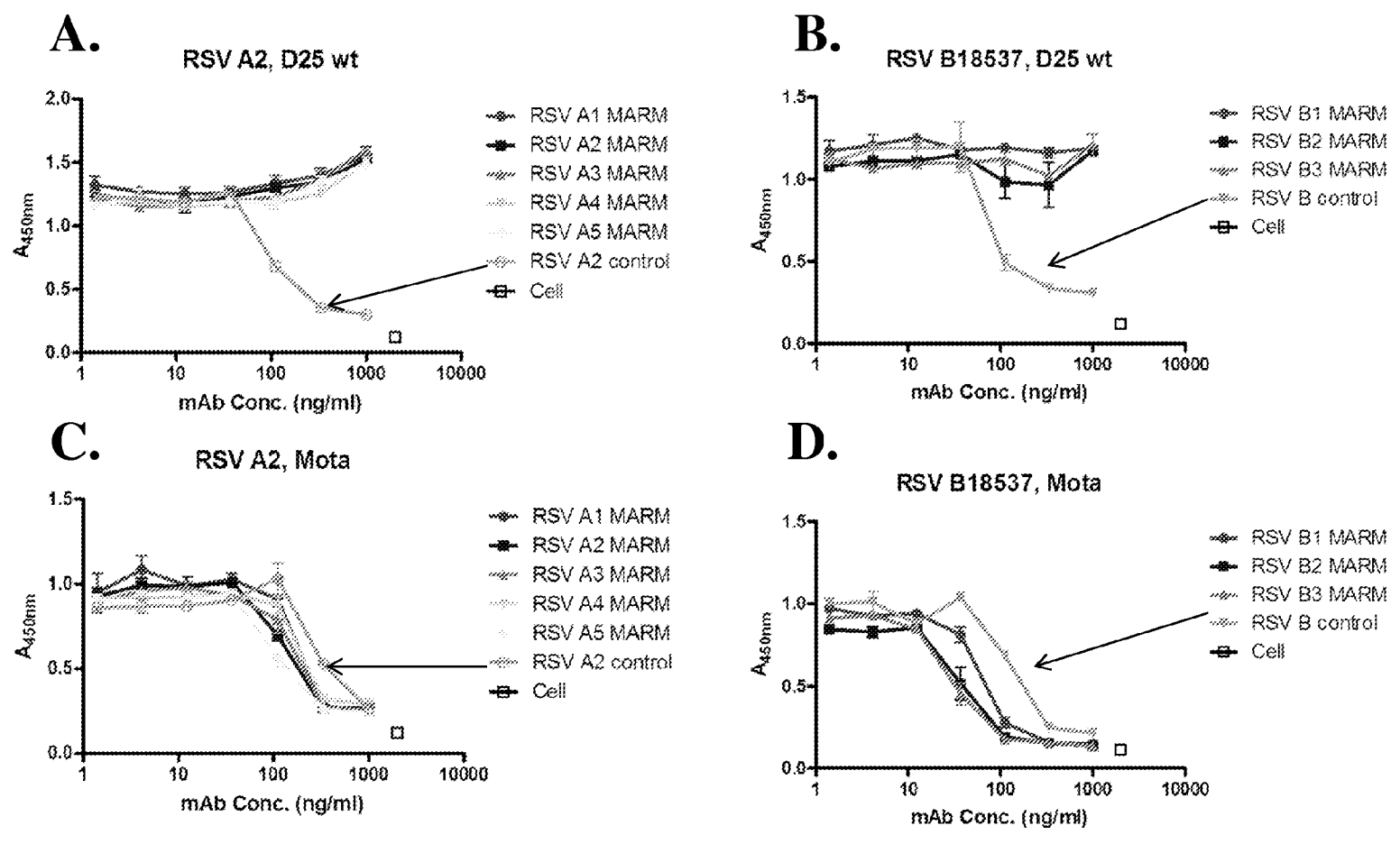

First, monoclonal antibody motavizumab was compared with D25 for neutralization activity on all the identified D25 MARMs. Dilutions of D25 or motavizumab (1-1000 ng/ml) were used for the neutralization assay, and the wild type RSV virus was used as a positive control. As shown in FIG. 11, motavizumab was able to neutralize both the wild-type RSV viruses and all the D25 MARMs, with 100 ng/ml or less motavizumab (FIGS. 11C and 11D), while D25 could only neutralize the wild-type viruses, but none of the MARMs, when 1-1000 ng/ml of D25 was used (FIGS. 11A and 11B).

Figure 12:
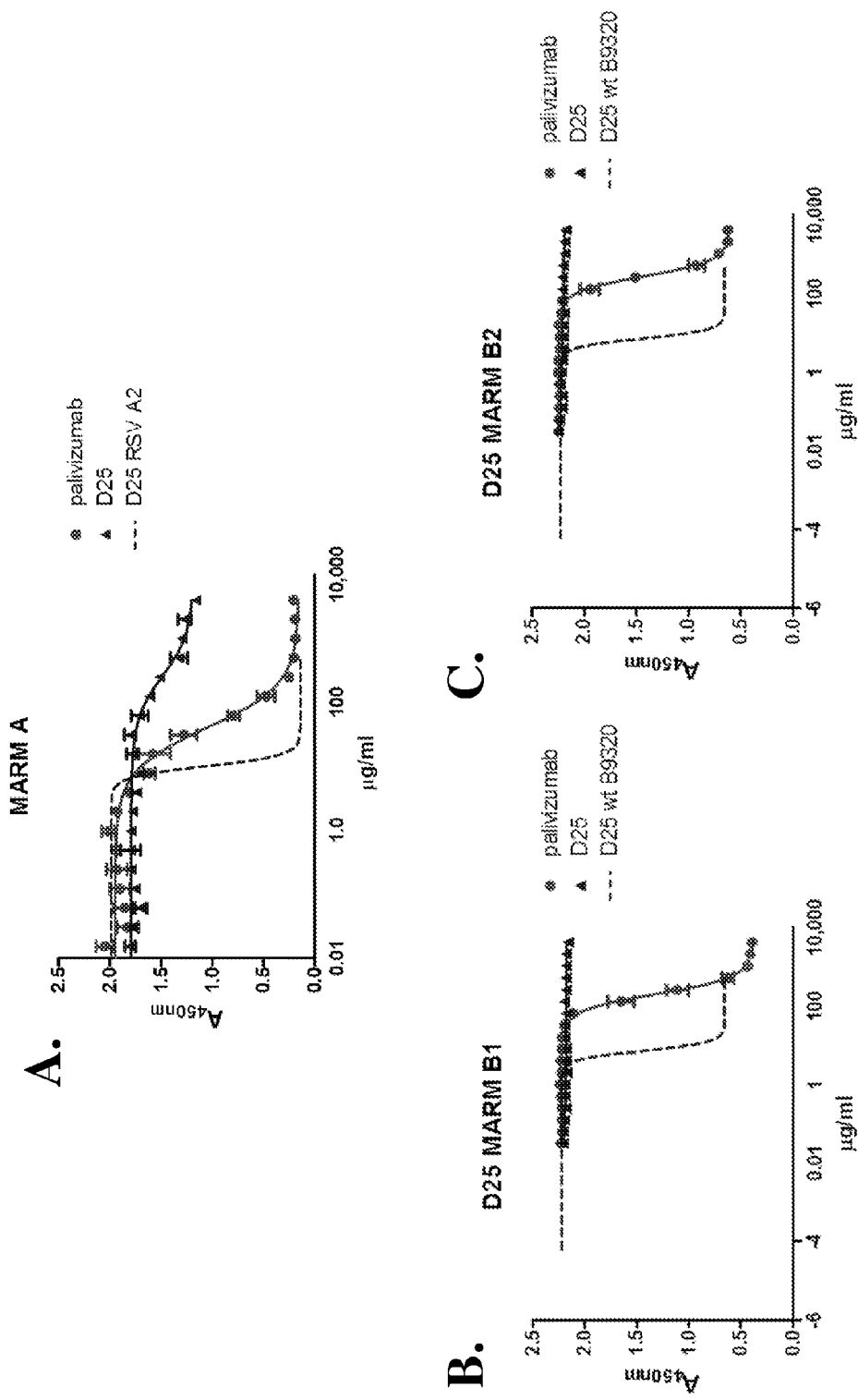

Similar experiments were performed comparing the neutralization activity of D25 and palivizumab. Dilutions of D25 or palivizumab (0.01 µg/ml to 10 mg/ml) were used for the microneutralization assay, and the wild type RSV virus was used as a positive control. As shown in FIG. 12, about 1 µg/ml of D25 was able to neutralize the wild type RSV virus, and around 100 µg/ml palivizumab was able to neutralize all three D25 MARMs. Both D25 MARM B1 and MARM B2 were completely insensitive to D25 neutralization (13B and 13C), indicating that the amino acids at position 201 and 204 are critical for D25 binding. On the other hand, D25 was able to neutralize the A2 MARM, but at minimally 100 fold of the concentration higher than what was needed to neutralize the wild type A2.

Example 8

Construction of the HR1 and the SK Epitope

As mentioned in Example 5, the identified region critical for D25 binding is C-terminal to the defined HR1 of the F protein that is important for the fusion process of the protein. Therefore, a construct containing the HR1 region (Table 1B) was made to test the D25 binding.

Figure 13:
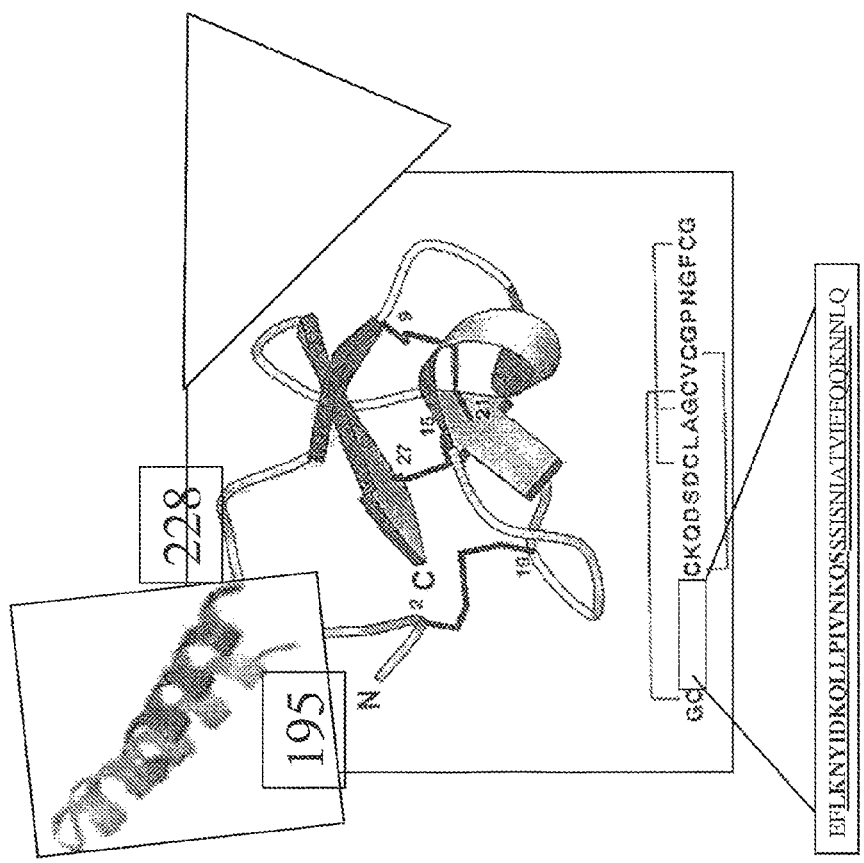

Furthermore, it appears that an extension of the C-terminus and a truncation of the N-terminus of the heptad repeat in a constrained construct may better reflect the pre-fusion structure of the D25 epitope. This construct termed SK-epitope contains the amino acids 195-228 of RSV-F protein from A2 in the first loop of the squash knot (SK) construct of the *Ecballium elaterium* trypsin inhibitor II (EETI-II), as illustrated in FIG. 13. Cysteine at position 212 of the RSV-F protein was substituted by serine.

These constructs were expressed in *E. coli* and the proteins were purified for binding assays.

Example 9

D25 Binds More Strongly to the SK-Epitope than to the HR1 Region

Biolayer Interometry Analysis was carried out to compare the binding affinity of D25 to the SK-epitope and to the HR1 region. D25 was applied to an anti-human IgG Fc capture sensor at concentrations ranging from 1.5625 nM to 100 nM. Sensors were moved to a kinetics buffer to establish a baseline then moved into a well containing either HR1 fragment or the SK-epitope construct.

Figure 14:
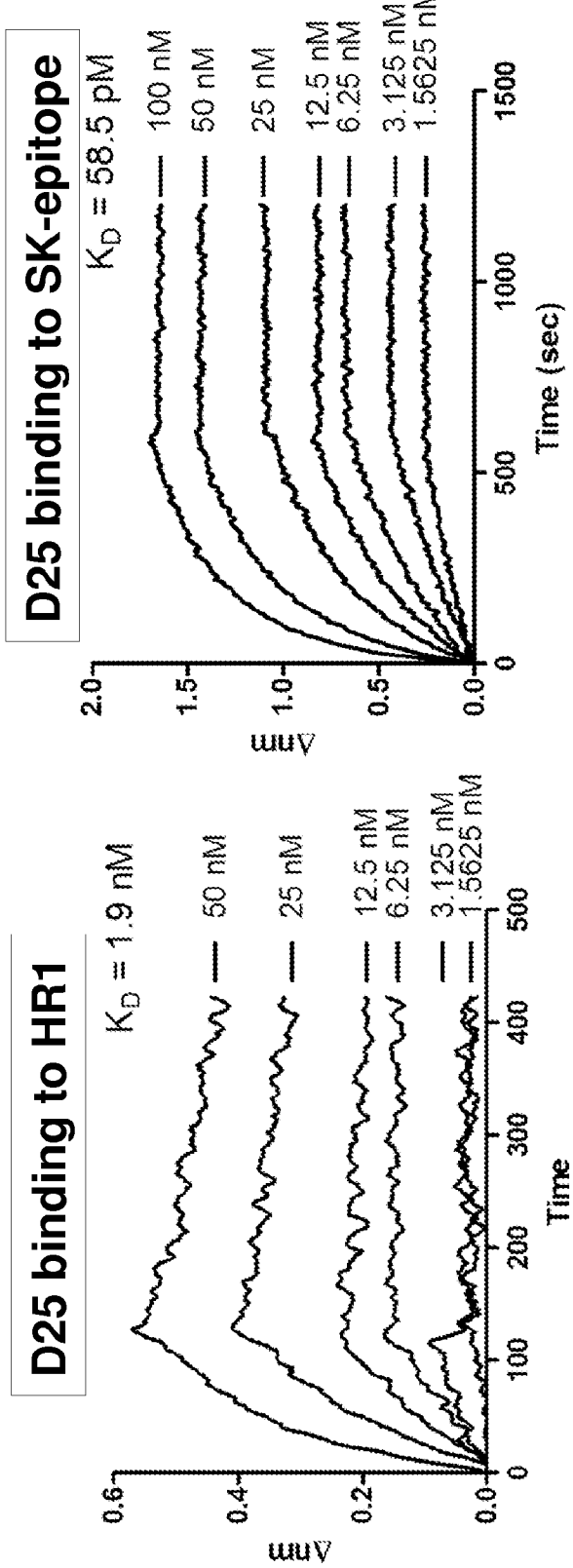

As shown in FIG. 14, D25 bound to both HR1 and the SK-epitope in a concentration dependent manner. However, D25 showed a higher affinity to SK-epitope than to HR1, as indicated by the calculated $K_D$ values (58.5 pM for SK-epitope vs. 1.9 nM for HR1).

\*\*\*

The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

What is claimed is:

1. A fusion protein comprising an isolated Respiratory Syncytial Virus (RSV) fusion (F) protein fragment fused to a heterologous non-RSV F protein polypeptide scaffold;
   wherein said non-RSV F protein polypeptide scaffold is a squash family protease inhibitor;
   wherein the isolated RSV F protein fragment consists of at least six consecutive amino acids of a peptide consisting of amino acids 195 to 228 of the RSV F protein; and
   wherein the inhibitor loop of the squash family protease inhibitor is replaced by the isolated RSV F protein fragment.

2. The fusion protein of claim 1, wherein said squash family protease inhibitor is the *Ecballium elaterium* trypsin inhibitor II (EETI-II).

3. A fusion protein comprising an isolated Respiratory Syncytial Virus (RSV) fusion (F) protein fragment fused to a heterologous non-RSV F protein polypeptide scaffold;
   wherein said non-RSV F protein polypeptide scaffold is a squash family protease inhibitor;
   wherein the isolated RSV F protein fragment consists of a peptide consisting of amino acids 195 to 228 of the RSV F protein; and
   wherein the inhibitor loop of the squash family protease inhibitor is replaced by the isolated RSV F protein fragment.

4. The fusion protein of claim 3, wherein said squash family protease inhibitor is the *Ecballium elaterium* trypsin inhibitor II (EETI-II).

5. The fusion protein of claim 3, wherein the cysteine at position 212 of the RSV F protein has been substituted by a serine.

6. The fusion protein of claim 3, wherein the RSV F protein comprises a human RSV subtype A F protein.

7. The fusion protein of claim 3, wherein the RSV F protein comprises a human RSV subtype B F protein.

8. The fusion protein of claim 6, wherein the human RSV subtype A comprises RSV A2.

9. The fusion protein of claim 7, wherein the human RSV subtype B comprises RSV 18537.

10. An immunogenic composition comprising the fusion protein of claim 3 and a pharmaceutically acceptable carrier.

11. The immunogenic composition of claim 10 further comprising an adjuvant.

12. The fusion protein of claim 1, wherein the isolated RSV F protein fragment consists of 8 to 10 consecutive amino acids of a peptide consisting of amino acids 195 to 228 of the RSV F protein.

13. A method of inducing an immune response to RSV in a subject, the method comprising administering an immunogenic composition of claim 10 to the subject.

14. The fusion protein of claim 1, wherein the isolated RSV F protein fragment consists of amino acids 195 to 228 of the RSV F protein.

15. The fusion protein of claim 3, wherein amino acids 195 to 228 of the RSV F protein consists of SEQ ID NO:7 or SEQ ID NO:9.

16. The fusion protein of claim 3 comprising SEQ ID NO:5.

17. A method for identifying an anti-RSV F protein antibody, comprising screening an antibody library for an antibody which binds to the fusion protein of claim 3, but does not bind to the heterologous non-RSV F protein polypeptide scaffold alone.

18. A fusion protein, the fusion protein comprising the polypeptide scaffold *Ecballium elaterium* trypsin inhibitor II (EETI-II), wherein the inhibitor loop of EETI-II is replaced by amino acids 1 to 34 of SEQ ID NO:7 or amino acids 1 to 34 of SEQ ID NO:9, and wherein the fusion protein is specifically bound by monoclonal antibody D25 or an antigen-binding fragment thereof.

19. A method for identifying an anti-RSV F protein antibody, comprising screening an antibody library for an antibody which binds to the fusion protein of claim 18, but does not bind to the heterologous non-RSV F protein polypeptide scaffold alone.

20. The fusion protein of claim 18, the fusion protein comprising the amino acid sequence SEQ ID NO: 5.

21. An immunogenic composition comprising the fusion protein of claim 18 and a pharmaceutically acceptable carrier and/or adjuvant.

22. A method of inducing an immune response to RSV in a subject, the method comprising administering an immunogenic composition of claim 18 to the subject.

23. The fusion protein of claim 3, wherein the fusion protein is specifically bound by monoclonal antibody D25 or an antigen-binding fragment thereof.

24. A method for identifying an anti-RSV F protein antibody, comprising screening an antibody library for an antibody which binds to the fusion protein of claim 1, but does not bind to the heterologous non-RSV F protein polypeptide scaffold alone.

25. An immunogenic composition comprising the fusion protein of claim 1 and a pharmaceutically acceptable carrier and/or adjuvant.

* * * * *

SEQUENCE LISTING

```
<160> NUMBER OF SEQ ID NOS: 14

<210> SEQ ID NO 1
<211> LENGTH: 574
<212> TYPE: PRT
<213> ORGANISM: Respiratory syncytial virus
<220> FEATURE:
<223> OTHER INFORMATION: RSV subtype A2, F protein

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
```

```
              290                 295                 300
Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 2
<211> LENGTH: 574
<212> TYPE: PRT
<213> ORGANISM: Respiratory syncytial virus
<220> FEATURE:
<223> OTHER INFORMATION: RSV subtype B, strain 18537, F protein

<400> SEQUENCE: 2

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
```

```
                    85                  90                  95
Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
        130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asn Asn Arg Leu Leu Pro Ile Val Asn
            195                 200                 205

Gln Gln Ser Cys Arg Ile Ser Asn Ile Glu Thr Val Ile Glu Phe Gln
        210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510
```

```
Leu His Asn Val Asn Thr Gly Lys Ser Thr Thr Asn Ile Met Ile Thr
            515                 520                 525
Thr Ile Ile Ile Val Ile Ile Val Val Leu Leu Ser Leu Ile Ala Ile
        530                 535                 540
Gly Leu Leu Leu Tyr Cys Lys Ala Lys Asn Thr Pro Val Thr Leu Ser
545                 550                 555                 560
Lys Asp Gln Leu Ser Gly Ile Asn Asn Ile Ala Phe Ser Lys
                565                 570

<210> SEQ ID NO 3
<211> LENGTH: 142
<212> TYPE: PRT
<213> ORGANISM: Artificial Sequence
<220> FEATURE:
<223> OTHER INFORMATION: Description of Artificial Sequence: Synthetic
      RSV subtype A2, F protein
<220> FEATURE:
<221> NAME/KEY: misc_feature
<222> LOCATION: (25)..(83)
<223> OTHER INFORMATION: HR1 region
<220> FEATURE:
<221> NAME/KEY: misc_feature
<222> LOCATION: (98)..(142)
<223> OTHER INFORMATION: HR2 region

<400> SEQUENCE: 3

Met Gly His His His His His His His His Ser Ser Gly His
1               5                   10                  15

Ile Asp Asp Asp Asp Lys His Met Ala Val Ser Lys Val Leu His Leu
                20                  25                  30

Glu Gly Glu Val Asn Lys Ile Lys Ser Ala Leu Leu Ser Thr Asn Lys
            35                  40                  45

Ala Val Val Ser Leu Ser Asn Gly Val Ser Val Leu Thr Ser Lys Val
        50                  55                  60

Leu Asp Leu Lys Asn Tyr Ile Asp Lys Gln Leu Leu Pro Ile Val Asn
65                  70                  75                  80

Lys Gln Ser Gly Gly Ser Gly Lys Gly Gly Thr Gly Gly Ser Gly
                85                  90                  95

Lys Asn Phe Tyr Asp Pro Leu Val Phe Pro Ser Asp Glu Phe Asp Ala
                100                 105                 110

Ser Ile Ser Gln Val Asn Glu Lys Ile Asn Gln Ser Leu Ala Phe Ile
            115                 120                 125

Arg Lys Ser Asp Glu Leu Leu His Asn Val Asn Ala Gly Lys
        130                 135                 140

<210> SEQ ID NO 4
<211> LENGTH: 83
<212> TYPE: PRT
<213> ORGANISM: Artificial Sequence
<220> FEATURE:
<223> OTHER INFORMATION: Description of Artificial Sequence: Synthetic
      RSV subtype A2, F protein
<220> FEATURE:
<221> NAME/KEY: misc_feature
<222> LOCATION: (25)..(83)
<223> OTHER INFORMATION: HR1 region

<400> SEQUENCE: 4

Met Gly His His His His His His His His Ser Ser Gly His
1               5                   10                  15

Ile Asp Asp Asp Asp Lys His Met Ala Val Ser Lys Val Leu His Leu
                20                  25                  30
```

```
Glu Gly Glu Val Asn Lys Ile Lys Ser Ala Leu Leu Ser Thr Asn Lys
        35                  40                  45

Ala Val Val Ser Leu Ser Asn Gly Val Ser Val Leu Thr Ser Lys Val
 50                  55                  60

Leu Asp Leu Lys Asn Tyr Ile Asp Lys Gln Leu Leu Pro Ile Val Asn
65                   70                  75                  80

Lys Gln Ser

<210> SEQ ID NO 5
<211> LENGTH: 80
<212> TYPE: PRT
<213> ORGANISM: Artificial Sequence
<220> FEATURE:
<223> OTHER INFORMATION: Description of Artificial Sequence: Synthetic
      RSV subtype A2, F protein, SK-Epitope
<220> FEATURE:
<221> NAME/KEY: misc_feature
<222> LOCATION: (19)..(35)
<223> OTHER INFORMATION: HR1 region
<220> FEATURE:
<221> NAME/KEY: misc_feature
<222> LOCATION: (17)..(52)
<223> OTHER INFORMATION: Epitope which replaces the inhibitor loop of
      the Ecballium elaterium trypsin inhibitor II (EETI-II)

<400> SEQUENCE: 5

Gln Pro Ala Met Ala Met Asp Ile Gly Ile Asn Ser Asp Pro Gly Cys
1               5                   10                  15

Glu Phe Leu Lys Asn Tyr Ile Asp Lys Gln Leu Leu Pro Ile Val Asn
            20                  25                  30

Lys Gln Ser Ser Ser Ile Ser Asn Ile Ala Thr Val Ile Glu Phe Gln
        35                  40                  45

Gln Lys Asn Asn Leu Gln Cys Lys Gln Asp Ser Asp Cys Leu Ala Gly
 50                  55                  60

Cys Val Cys Gly Pro Asn Gly Phe Cys Gly Val Asp Lys Leu Ala Ala
65                   70                  75                  80

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Leu Glu His His His His His His
1               5

<210> SEQ ID NO 7
<211> LENGTH: 34
<212> TYPE: PRT
<213> ORGANISM: Respiratory syncytial virus
<220> FEATURE:
<223> OTHER INFORMATION: RSV wild-type A, F protein

<400> SEQUENCE: 7

Leu Lys Asn Tyr Ile Asp Lys Gln Leu Leu Pro Ile Val Asn Lys Gln
1               5                   10                  15

Ser Cys Ser Ile Ser Asn Ile Glu Thr Val Ile Glu Phe Gln Gln Lys
            20                  25                  30

Asn Asn
```

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
      RSV subtype A, F protein, D25 monoclonal antibody
      resistant mutant (MARM) A1

<400> SEQUENCE: 8

Leu Lys Asn Tyr Ile Asp Lys Gln Leu Leu Pro Ile Val Tyr Lys Gln
1               5                   10                  15

Ser Cys Ser Ile Ser Asn Ile Glu Thr Val Ile Glu Phe Gln Gln Lys
            20                  25                  30

Asn Asn

<210> SEQ ID NO 9
<211> LENGTH: 34
<212> TYPE: PRT
<213> ORGANISM: Respiratory syncytial virus
<220> FEATURE:
<223> OTHER INFORMATION: RSV wild-type B, F protein

<400> SEQUENCE: 9

Leu Lys Asn Tyr Ile Asn Asn Arg Leu Leu Pro Ile Val Asn Gln Gln
1               5                   10                  15

Ser Cys Arg Ile Ser Asn Ile Glu Thr Val Ile Glu Phe Gln Gln Met
            20                  25                  30

Asn Ser

<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence: Synthetic
      RSV subtype B, F protein, D25 monoclonal antibody
      resistant mutant (MARM) B1

<400> SEQUENCE: 10

Leu Lys Asn Tyr Ile Asn Asp Arg Leu Leu Pro Ile Val Asn Gln Gln
1               5                   10                  15

Ser Cys Arg Ile Ser Asn Ile Glu Thr Val Ile Glu Phe Gln Gln Met
            20                  25                  30

Asn Ser

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      RSV subtype B, F protein, D25 monoclonal antibody
      resistant mutant (MARM) B2

<400> SEQUENCE: 11

Leu Lys Asn Tyr Ile Asn Asn Arg Leu Val Pro Ile Val Asn Gln Gln
1               5                   10                  15

Ser Cys Arg Ile Ser Asn Ile Glu Thr Val Ile Glu Phe Gln Gln Met
            20                  25                  30

Asn Ser

<210> SEQ ID NO 12
<211> LENGTH: 574
<212> TYPE: PRT
<213> ORGANISM: Artificial Sequence
<220> FEATURE:
<223> OTHER INFORMATION: Description of Artificial Sequence: Synthetic
    RSV subtype A, F protein, D25 monoclonal antibody
    resistant mutant (MARM) A1
<220> FEATURE:
<221> NAME/KEY: SIGNAL
<222> LOCATION: (1)..(28)
<223> OTHER INFORMATION: signal peptide
<220> FEATURE:
<221> NAME/KEY: misc_feature
<222> LOCATION: (195)..(228)
<223> OTHER INFORMATION: conformational epitope in the wild-type RSV F
    A2 protein

<400> SEQUENCE: 12

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Tyr
        195                 200                 205

Lys Gln Ser Cys Ser Ile Ser Asn Ile Ala Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

-continued

```
Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Ile Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570
```

<210> SEQ ID NO 13
<211> LENGTH: 574
<212> TYPE: PRT
<213> ORGANISM: Artificial Sequence
<220> FEATURE:
<223> OTHER INFORMATION: Description of Artificial Sequence: Synthetic
      RSV subtype B, F protein, D25 monoclonal antibody resistant
      mutant (MARM) B1
<220> FEATURE:
<221> NAME/KEY: SIGNAL
<222> LOCATION: (1)..(22)
<223> OTHER INFORMATION: signal peptide
<220> FEATURE:
<221> NAME/KEY: misc_feature
<222> LOCATION: (195)..(228)
<223> OTHER INFORMATION: conformational epitope in the wild-type RSV F
      protein

<400> SEQUENCE: 13

```
Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45
```

```
Arg Thr Gly Trp Tyr Thr Ser Val Ile Thr Ile Glu Leu Ser Asn Ile
     50                  55                  60

Lys Glu Thr Lys Cys Asn Gly Thr Asp Thr Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Asn Thr Pro Ala Ala Asn Asn Arg Ala Arg Arg Glu Ala Pro
             100                 105                 110

Gln Tyr Met Asn Tyr Thr Ile Asn Thr Thr Lys Asn Leu Asn Val Ser
             115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                 165                 170                 175

Ala Val Val Ser Leu Ser Asn Gly Val Ser Val Leu Thr Ser Lys Val
             180                 185                 190

Leu Asp Leu Lys Asn Tyr Ile Asn Asp Arg Leu Leu Pro Ile Val Asn
             195                 200                 205

Gln Gln Ser Cys Arg Ile Ser Asn Ile Glu Thr Val Ile Glu Phe Gln
             210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                 245                 250                 255

Leu Leu Ser Leu Ile Asn Asp Met Pro Ile Thr Asn Asp Gln Lys Lys
             260                 265                 270

Leu Met Ser Ser Asn Val Gln Ile Val Arg Gln Gln Ser Tyr Ser Ile
             275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                 325                 330                 335

Thr Asp Arg Gly Trp Tyr Cys Asp Asn Ala Gly Ser Val Ser Phe Phe
             340                 345                 350

Pro Gln Ala Asp Thr Cys Lys Val Gln Ser Asn Arg Val Phe Cys Asp
             355                 360                 365

Thr Met Asn Ser Leu Thr Leu Pro Ser Glu Val Ser Leu Cys Asn Thr
             370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                 405                 410                 415

Tyr Gly Lys Thr Lys Cys Thr Ala Ser Asn Lys Asn Arg Gly Ile Ile
             420                 425                 430

Lys Thr Phe Ser Asn Gly Cys Asp Tyr Val Ser Asn Lys Gly Val Asp
             435                 440                 445

Thr Val Ser Val Gly Asn Thr Leu Tyr Val Asn Lys Leu Glu Gly
             450                 455                 460

Lys Asn Leu Tyr Val Lys Gly Glu Pro Ile Ile Asn Tyr Tyr Asp Pro
```

-continued

```
                465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Ile Met Ile Thr
                515                 520                 525

Thr Ile Ile Ile Val Ile Ile Val Val Leu Leu Ser Leu Ile Ala Ile
                530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 14
<211> LENGTH: 574
<212> TYPE: PRT
<213> ORGANISM: Artificial Sequence
<220> FEATURE:
<223> OTHER INFORMATION: Description of Artificial Sequence: Synthetic
      RSV subtype B, F protein, D25 monoclonal antibody resistant
      mutant (MARM) B2
<220> FEATURE:
<221> NAME/KEY: SIGNAL
<222> LOCATION: (1)..(22)
<223> OTHER INFORMATION: signal peptide
<220> FEATURE:
<221> NAME/KEY: misc_feature
<222> LOCATION: (195)..(228)
<223> OTHER INFORMATION: conformational epitope in the wild-type RSV F
      protein

<400> SEQUENCE: 14

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
                20                  25                  30

Tyr Gln Ser Thr Cys Ser Ala Val Ser Arg Gly Tyr Phe Ser Ala Leu
            35                  40                  45

Arg Thr Gly Trp Tyr Thr Ser Val Ile Thr Ile Glu Leu Ser Asn Ile
        50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
        130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Arg Leu Val Pro Ile Val Asn
        195                 200                 205
```

```
Gln Gln Ser Cys Arg Ile Ser Asn Ile Glu Thr Val Ile Glu Phe Gln
    210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```